United States Patent
Nagaoka et al.

(10) Patent No.: US 9,842,999 B2
(45) Date of Patent: Dec. 12, 2017

(54) BENZOTRIAZOLE DERIVATIVE AND AN ORGANIC ELECTROLUMINESCENT DEVICE

(71) Applicant: HODOGAYA CHEMICAL CO., LTD., Tokyo (JP)

(72) Inventors: Makoto Nagaoka, Tokyo (JP); Shigetaka Numazawa, Tokyo (JP); Kanae Otsuka, Tokyo (JP); Shigeru Kusano, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 24 days.

(21) Appl. No.: 14/908,310

(22) PCT Filed: Jul. 24, 2014

(86) PCT No.: PCT/JP2014/069574
§ 371 (c)(1),
(2) Date: Jan. 28, 2016

(87) PCT Pub. No.: WO2015/016135
PCT Pub. Date: Feb. 5, 2015

(65) Prior Publication Data
US 2016/0164001 A1  Jun. 9, 2016

(30) Foreign Application Priority Data

Jul. 29, 2013 (JP) .................. 2013-156295

(51) Int. Cl.
*H01L 51/50* (2006.01)
*H01L 51/00* (2006.01)
(Continued)

(52) U.S. Cl.
CPC ........ *H01L 51/0072* (2013.01); *C07D 401/10* (2013.01); *C07D 401/14* (2013.01);
(Continued)

(58) Field of Classification Search
None
See application file for complete search history.

(56) References Cited

U.S. PATENT DOCUMENTS 4,119,634 A  10/1978 Schroeder
5,869,199 A  2/1999 Kido
(Continued)

FOREIGN PATENT DOCUMENTS

EP  2 409 974  1/2012
JP  53-21222  2/1978
(Continued)

OTHER PUBLICATIONS

International Search Report issued in PCT/JP2014/069574, dated Sep. 9, 2014.
(Continued)

*Primary Examiner* — Gregory D Clark
(74) *Attorney, Agent, or Firm* — Greenblum & Bernstein. P.L.C.

(57) ABSTRACT

A Benzotriazole derivative represented by the following general formula (1),

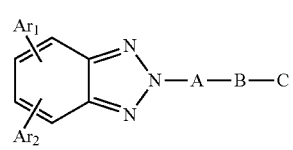

(1)

wherein,
$Ar^1$ is a monovalent aromatic hydrocarbon group or aromatic heterocyclic group,
(Continued)

9: CATHODE
8: ELECTRON INJECTION LAYER
7: ELECTRON-TRANSPORTING LAYER
6: HOLE-BLOCKING LAYER
5: LUMINOUS LAYER
4: HOLE-TRANSPORTING LAYER
3: HOLE INJECTION LAYER
2: TRANSPARENT ANODE
1: GLASS SUBSTRATE $Ar^2$ is a hydrogen atom, a deuterium atom, or a monovalent aromatic hydrocarbon group or aromatic heterocyclic group, A is a divalent aromatic hydrocarbon group or aromatic heterocyclic group, B is a divalent condensed polycyclic aromatic hydrocarbon group or a single bond, and C is a monovalent aromatic heterocyclic group, and wherein if A is a phenylene group, B is a divalent condensed polycyclic aromatic hydrocarbon group or C is a monovalent aromatic heterocyclic group other than a pyridyl group.

11 Claims, 3 Drawing Sheets

(51) Int. Cl.
  *C07D 401/10*  (2006.01)
  *C07D 401/14*  (2006.01)

(52) U.S. Cl.
  CPC ...... *H01L 51/0052* (2013.01); *H01L 51/0058* (2013.01); *H01L 51/0067* (2013.01); *H01L 51/5012* (2013.01); *H01L 51/5072* (2013.01); *H01L 51/5096* (2013.01)

(56) References Cited

U.S. PATENT DOCUMENTS

| | | | |
|---|---|---|---|
| 6,878,469 | B2 | 4/2005 | Yoon et al. |
| 2003/0165715 | A1 | 9/2003 | Yoon et al. |
| 2005/0175856 | A1 | 8/2005 | Rogers et al. |
| 2008/0027226 | A1 | 1/2008 | Rogers et al. |
| 2010/0073603 | A1 | 3/2010 | Akino |
| 2012/0012831 | A1 | 1/2012 | Yokoyama et al. |
| 2014/0374721 | A1* | 12/2014 | Yokoyama ........... C07D 401/14 257/40 |

FOREIGN PATENT DOCUMENTS

| | | |
|---|---|---|
| JP | 2734341 | 1/1998 |
| KR | 10-2012-0072784 | 7/2012 |
| WO | 03/060956 | 7/2003 |
| WO | 03/105538 | 12/2003 |
| WO | 2005/054212 | 6/2005 |
| WO | 2008/096736 | 8/2008 |
| WO | 2010/107074 | 9/2010 |
| WO | 2013/054764 | 4/2013 |

OTHER PUBLICATIONS

Musubu Ichikawa et al., "Bipyridyl-substituted benzo [1,2,3] triazoles as a thermally stable electron transporting material for organic light-emitting devices"; Journal of Materials Chemistry, vol. 21, No. 32, XP055130667; Jul. 4, 2011; pp. 11791-11799.

Extended European Search Report issued in Patent Application No. 14832687.9, dated Feb. 24, 2017.

\* cited by examiner

9: CATHODE
8: ELECTRON INJECTION LAYER
7: ELECTRON-TRANSPORTING LAYER
6: HOLE-BLOCKING LAYER
5: LUMINOUS LAYER
4: HOLE-TRANSPORTING LAYER
3: HOLE INJECTION LAYER
2: TRANSPARENT ANODE
1: GLASS SUBSTRATE

BENZOTRIAZOLE DERIVATIVE AND AN ORGANIC ELECTROLUMINESCENT DEVICE

FIELD OF THE INVENTION

This invention relates to novel benzotriazole derivatives and to organic electroluminescent devices that have an organic layer containing the above derivatives between the electrodes.

BACKGROUND ART

An organic electroluminescent device (hereinafter often called an organic EL device) is a spontaneously luminous device which features higher brightness and higher legibility than those of the liquid crystal devices enabling vivid display to be attained and has, therefore, been vigorously studied.

In 1987, C. W. Tang et al. of Eastman Kodak Company have developed a device of a layer-laminated structure comprising various kinds of materials to bear individual roles, and have put an organic EL device using organic materials into a practical use. The above organic EL device is constituted by laminating layers of a fluorescent body capable of transporting electrons and an organic material capable of transporting holes. Upon injecting both electric charges into the layer of the fluorescent body to emit light, the device is capable of attaining a brightness of as high as 1000 cd/m$^2$ or more with a voltage of not higher than 10 V.

So far, very many improvements have been made to put the organic EL device to practical use. For example, the organic EL device has been widely known having a structure comprising an anode, a hole injection layer, a hole-transporting layer, a luminous layer, an electron-transporting layer, an electron injection layer and a cathode which are arranged in this order on a substrate more finely dividing the roles required for the organic layers between the electrodes than ever before. The device of this kind is achieving a high efficiency and a high durability.

To further improve the luminous efficiency, attempts have been made to utilize triplet excitons and study has been forwarded to utilize a phosphorescent luminous compound.

In the organic EL device, the electric charges injected from the two electrodes recombine together in the luminous layer to emit light. Here, however, what is important is that how efficiently both electric charges of holes and electrons be handed over to the luminous layer. Upon increasing the injection of electrons and their mobility, the holes and electrons recombine together at an increased probability. Further, upon confining the excitons formed in the luminous layer, a high luminous efficiency can be attained. Therefore, the electron-transporting material plays an important role, and it has been urged to provide an electron-transporting material that has a large electron-injection property, a large electron mobility, a high hole-blocking capability and a large durability against the holes.

As for the life of the device, further, the heat resistance and amorphousness of the material also serve as important factors. The material having small heat resistance is subject to be thermally decomposed even at low temperatures due to the heat generated when the device is driven, and is deteriorated. The material having low amorphousness permits the thin film thereof to be crystallized in short periods of time and, therefore, the device to be deteriorated. Therefore, the material to be used must have large heat resistance and good amorphousness.

Tris(8-hydroxyquinoline)aluminum (hereinafter abbreviated as Alq$_3$) which is a representative luminous material has also been generally used as an electron-transporting material having, however, a low electron mobility and a work function of 5.6 eV and, therefore, having a hole-blocking capability which is far from satisfactory.

A method of inserting a hole-blocking layer is one of the measures for preventing the holes from partly passing through the luminous layer to improve the probability of recombination of the electric charge in the luminous layer.

As a hole-blocking material used for forming the hole-blocking layer, for example, there have been known triazole derivatives (see, for example, a patent document 1), bathocuproin (hereinafter abbreviated as BCP) and a mixed ligand complex of aluminum [aluminum(III)bis(2-methyl-8-quinolinato)-4-phenyl phenolate (hereinafter abbreviated as BAlq).

As an electron-transporting material having excellent hole-blocking property, further, there has been proposed a 3-(4-biphenylyl)-4-phenyl-5-(4-t-butylphenyl)-1,2,4-triazole (hereinafter abbreviated as TAZ) (see, for example, a patent document 2).

The TAZ has a work function of as large as 6.6 eV and a large hole-blocking power, and is used for forming an electron-transporting hole-blocking layer that is laminated on the cathode side of a fluorescent luminous layer or a phosphorescent luminous layer prepared by vacuum evaporation or by coating and, therefore, contributes to improving the efficiency of the organic EL devices.

However, a big problem of the TAZ was its low electron-transporting capability. To fabricate an organic EL device, therefore, the TAZ had to be used in combination with an electron-transporting material having a higher electron-transporting capability.

Further, the BCP, too, has a work function of as large as 6.7 eV and a large hole-blocking power but a glass transition point (Tg) of as low as 83° C. In the form of a thin film, therefore, the BCP lacks stability and cannot be said to work as a hole-blocking layer to a sufficient degree.

That is, the above-mentioned materials all lack stability if they are used in the form of a film or are not capable of blocking the holes to a sufficient degree. In order to improve characteristics of the organic EL devices, therefore, it has been desired to provide an organic compound that excels in electron injection/transporting capability and in hole-blocking power, and features high stability in the form of a thin film.

PRIOR ART DOCUMENTS

Patent Documents

Patent document 1: Japanese Patent No. 2734341
Patent document 2: WO2003/060956

OUTLINE OF THE INVENTION

Problems that the Invention is to Solve

The object of the present invention is to provide an organic compound that excels in electron injection/transporting capability, features a high hole-blocking power and a high stability in the form of a thin film, and can be used as a material for producing highly efficient and highly durable organic electroluminescent devices, and to provide highly efficient and highly durable organic electroluminescent devices formed by using the above compound.

Means for Solving the Problems

According to the present invention, there is provided a benzotriazole derivative represented by the following general formula (1),

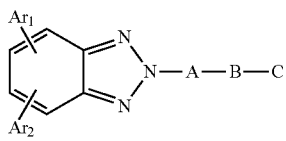

wherein,
$Ar^1$ is a monovalent aromatic hydrocarbon group or aromatic heterocyclic group,
$Ar^2$ is a hydrogen atom, a deuterium atom, or a monovalent aromatic hydrocarbon group or aromatic heterocyclic group,
A is a divalent aromatic hydrocarbon group or aromatic heterocyclic group,
B is a divalent condensed polycyclic aromatic hydrocarbon group or a single bond, and
C is a monovalent aromatic heterocyclic group, and wherein if A is a phenylene group, B is a divalent condensed polycyclic aromatic hydrocarbon group or C is a monovalent aromatic heterocyclic group other than a pyridyl group.

According to the present invention, further, there is provided an organic electroluminescent device having a pair of electrodes and at least one organic layer held therebetween, wherein at least the one organic layer contains the benzotriazole derivative.

In the organic EL device, the organic layer containing the benzotriazole derivative may be any one of an electron-transporting layer, a hole-blocking layer, a luminous layer or an electron injection layer.

Effects of the Invention

As will be understood from the above general formula (1), the benzotriazole derivatives of the invention represented by the general formula (1) are novel compounds having a benzotriazole ring, and feature the following properties.
(A) The electrons can be favorably injected.
(B) The electrons migrate at a high rate.
(C) The holes can be blocked favorably.
(D) Remains stable in a thin-film state.
(E) Excellent heat resistance.

Therefore, the benzotriazole derivatives of the invention remain stable in the form of a thin film, can be used as an organic layer that is provided between the electrodes of the organic EL device, and are capable of imparting the following properties to the organic EL device:
(F) A high luminous efficiency and a high power efficiency.
(G) A low luminescence start voltage.
(H) A low practical driving voltage.
(I) A long service life (excellent durability).

For instance, the benzotriazole derivatives of the invention feature high electron injection drift speed. If the benzotriazole derivatives are used as a material for constituting the electron injection layer and/or the electron-transporting layer of the organic EL device, therefore, the efficiency is improved for transporting the electrons from the electron-transporting layer into the luminous layer, the luminous efficiency is improved, the driving voltage is lowered, and the durability of the organic EL device can be improved.

Further, if the benzotriazole derivatives of the invention are used as a material for constituting the hole-blocking layer of the organic EL device, it is made possible to realize a high luminous efficiency owing to their excellent hole-blocking power, electron-transporting property and stability in the form of a thin film and, at the same time, to lower the driving voltage, to improve durability against the electric current and, therefore, to attain improved maximum brightness of the organic EL device.

To utilize excellent electron transporting capability and a wide band gap of the benzotriazole derivatives of the invention, further, the benzotriazole derivatives are used as a host material to carry a fluorescent material or a luminous phosphor called dopant thereon so as to form a luminous layer. This makes it possible to realize the organic EL device that drives on a decreased voltage and features an improved the luminous efficiency.

As described above, by using the benzotriazole derivatives of the invention as a material for constituting organic layers of the organic EL device to utilize their characteristics, it is made possible to confine the excitons formed in the luminous layer, to improve the probability of recombining the holes with the electrons, to attain a high luminous efficiency, to lower the driving voltage and to realize a high efficiency and a high degree of durability.

MODES FOR CARRYING OUT THE INVENTION

Figure 1:
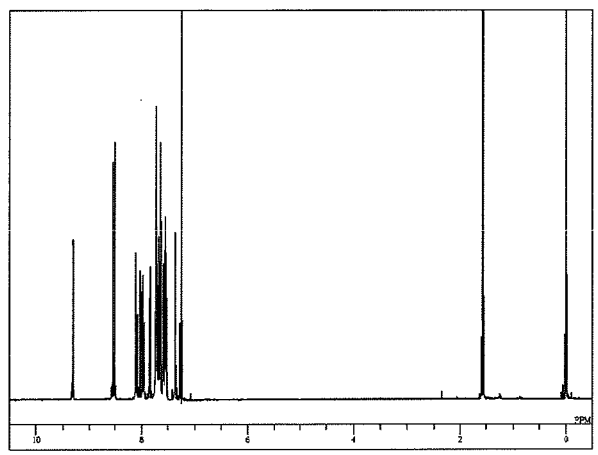
FIG. 1 is a $^1$H-NMR chart of a compound (compound 12) of Example 1.

The benzotriazole derivatives of the present invention are represented by the following general formula (1) and have a structure in which an aromatic hydrocarbon group or an aromatic heterocyclic group is bonded to a nitrogen atom in the benzotriazole ring.

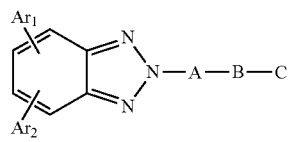

In the above general formula (1), $Ar^1$ is a monovalent aromatic hydrocarbon group or aromatic heterocyclic group, and $Ar^2$ is a hydrogen atom, a deuterium atom, or a monovalent aromatic hydrocarbon group or aromatic heterocyclic group.

Both the monovalent aromatic hydrocarbon group and the monovalent aromatic heterocyclic group represented by $Ar^1$ and $Ar^2$ may have a monocyclic structure or a polycyclic structure, or may have a condensed polycyclic structure.

As the monovalent aromatic hydrocarbon group, there can be preferably used phenyl group, biphenylyl group, terphenylyl group, tetrakisphenyl group, stylyl group, naphthyl group, anthracenyl group, acenaphthenyl group, phenanthryl group, fluorenyl group, indenyl group and pyrenyl group, and particularly preferably, phenyl group, biphenylyl group, terphenylyl group, naphthyl group, anthracenyl group, phenanthryl group and fluorenyl group.

As the monovalent aromatic heterocyclic group, further, there can be preferably used pyridyl group, triazinyl group, pyrimidinyl group, furyl group, pyrolyl group, thienyl group, quinolyl group, isoquinolyl group, benzofuranyl group, benzothienyl group, indolyl group, carbazolyl group, carbolinyl group, benzoxazolyl group, benzthiazolyl group, quinoxalyl group, benzimidazolyl group, pyrazolyl group, dibenzofuranyl group, dibenzothienyl group, naphthylydinyl group, phenanthrolynyl group and acrydinyl group, and particularly preferably, pyridyl group, carbazolyl group and dibenzofuranyl group.

Further, the above monovalent aromatic hydrocarbon group and the monovalent aromatic heterocyclic group may have a substituent.

As the substituent, there can be exemplified deuterium atom; cyano group; hydroxyl group; nitro group; halogen atoms such as fluorine atom, chlorine atom and the like atoms; alkyl groups having 1 to 6 carbon atoms, such as methyl group, ethyl group, n-propyl group, isopropyl group, n-butyl group, isobutyl group, tert-butyl group, n-pentyl group, isopentyl group, neopentyl group and n-hexyl group; cycloalkyl groups having 5 to 10 carbon atoms, such as cyclopentyl group and cyclohexyl group; alkyloxy groups having 1 to 6 carbon atoms, such as methyloxy group, ethyloxy group and propyloxy group; di-substituted amino groups having, as substituents, alkyl groups that have 1 to 6 carbon atoms; aromatic hydrocarbon groups such as phenyl group, biphenylyl group, terphenylyl group, tetrakisphenyl group, styryl group, naphthyl group, anthracenyl group, acenaphthenyl group, phenanthryl group, fluorenyl group, indenyl group and pyrenyl group; and aromatic heterocyclic groups such as pyridyl group, triazinyl group, pyrimidinyl group, quinolyl group, isoquinolyl group, indolyl group, pyridoindolyl group, carbazolyl group, carbolynyl group, quinoxalyl group, benzimidazolyl group, pyrazolyl group, phenanthrolynyl group and acridinyl group. Further, these substituents may be those having a substituent exemplified above like the trifluoromethyl group.

Moreover, the above substituents may be bonded together via a single bond, via a substituted or unsubstituted methylene group, or via an oxygen atom or a sulfur atom to form a ring.

Among them, particularly preferred substituents are aromatic hydrocarbon groups and aromatic heterocyclic groups, and further preferred substituents are phenyl group, biphenylyl group, naphthyl group, anthracenyl group, phenanthryl group, fluorenyl group, pyrenyl group, pyridyl group, triazinyl group, pyrimidinyl group, quinolyl group, isoquinolyl group, indolyl group, carbazolyl group, quinoxalyl group, benzimidazolyl group, pyrazolyl group, phenanthrolynyl group and acrydinyl group. The most preferred substituents are phenyl group, naphthyl group, anthracenyl group, pyridyl group, quinolyl group and isoquinolyl group.

In the above general formula (1), further, A is a divalent aromatic hydrocarbon group or aromatic heterocyclic group, B is a divalent condensed polycyclic aromatic hydrocarbon group or a single bond, and C is a monovalent aromatic heterocyclic group, and wherein if A is a phenylene group, B is a divalent condensed polycyclic aromatic hydrocarbon group or C is a monovalent aromatic heterocyclic group other than a pyridyl group.

The divalent aromatic hydrocarbon group and the divalent aromatic heterocyclic group represented by A may, respectively, have a monocyclic structure or a polycyclic structure, or may have a condensed polycyclic structure.

As the divalent aromatic hydrocarbon groups, there can be exemplified the groups of the following aromatic hydrocarbon compounds having an aromatic ring from which two hydrogen atoms have been removed; i.e., benzene, biphenyl, terphenyl, tetrakisphenyl, styrene, naphthalene, anthracene, acenaphthalene, fluorene, phenanthrene, indane, pyrene, etc.

As the divalent aromatic heterocyclic groups, further, there can be exemplified the groups of the following aromatic heterocyclic compounds having a heterocyclic group from which two hydrogen atoms have been removed; i.e., pyridine, pyrimidine, triazine, furane, pyran, thiophene, quinolone, isoquioline, benzofurane, benzothiophene, indoline, carbazole, carboline, benzoxazole, benzthiazole, quinoxaline, benzimidazole, pyrazole, dibenzofurane, dibenzothiophene, naphthyridine, phenanthroline and acridinene.

The above divalent aromatic hydrocarbon group and aromatic heterocyclic group may have a substituent which may be the same as the substituent possessed by the monovalent aromatic groups mentioned above. Namely, there can be exemplified deuterium atom; cyano group; hydroxyl group; nitro group; halogen atoms such as fluorine atom, chlorine atom and the like atoms; alkyl groups having 1 to 6 carbon atoms, such as methyl group, ethyl group, n-propyl group, isopropyl group, n-butyl group, isobutyl group, tert-butyl group, n-pentyl group, isopentyl group, neopentyl group and n-hexyl group; cycloalkyl groups having 5 to 10 carbon atoms, such as cyclopentyl group and cyclohexyl group; alkyloxy groups having 1 to 6 carbon atoms, such as methyloxy group, ethyloxy group and propyloxy group; di-substituted amino groups having, as substituents, alkyl groups that have 1 to 6 carbon atoms; aromatic hydrocarbon groups such as phenyl group, biphenylyl group, terphenylyl group, tetrakisphenyl group, styryl group, naphthyl group, anthracenyl group, acenaphthenyl group, phenanthryl group, fluorenyl group, indenyl group and pyrenyl group; and aromatic heterocyclic groups such as pyridyl group, pyridoindolyl group, quinolyl group and benzothiazolyl group. These substituents may further have a substituent exemplified above like the trifluoromethyl group.

Moreover, the above substituents may be bonded together via a single bond, via a substituted or unsubstituted methylene group, or via an oxygen atom or a sulfur atom to form a ring.

In the invention, the group A is, particularly preferably, a divalent aromatic hydrocarbon group and, specifically, phenylene group, naphthalenylene group, anthracenylene group, fluorenylene group, phenanthrenylene group or pyrenylene group. These groups may have a substituent described above but, most preferably, has no substituent.

In the general formula (1), further, B represents a divalent condensed polycyclic aromatic hydrocarbon group or a single bond. Here, as the divalent condensed polycyclic aromatic hydrocarbon groups, there can be exemplified those having a condensed polycyclic structure among the above-mentioned divalent aromatic hydrocarbon groups. Specifically preferably, there can be used naphthalenylene group, anthracenylene group, acenaphthalenylene group, fluorenylene group, phenanthrenylene group, indanylene group and pyrenylene group.

These divalent condensed polycyclic aromatic hydrocarbon groups, too, may have a substituent similar to the substituent which may be possessed by the above-mentioned monovalent aromatic heterocyclic groups.

In the general formula (1), further, C is a monovalent aromatic heterocyclic group which may be the same as the monovalent aromatic heterocyclic group represented by $Ar^1$ and $Ar^2$. Preferably, however, there can be used those having a nitrogen atom as the hetero atom.

As the monovalent aromatic heterocyclic group containing the nitrogen atom, there can be exemplified pyridyl group, triazinyl group, pyrimidinyl group, pyrrolyl group, quinolyl group, isoquinolyl group, indolyl group, carbazolyl group, carbolinyl group, benzoxazolyl group, benzothiazolyl group, quinoxalyl group, benzimidazolyl group, pyrazolyl group, naphthylydinyl group, phenanthrolynyl group and acrydinyl group. Among these nitrogen-containing heterocyclic groups, particularly preferred are pyridyl group, pyrimidinyl group, quinolyl group, isoquinolyl group, indolyl group, carbolynyl group, quinoxalyl group, benzimidazolyl group, naphthylidinyl group, phenanthrolynyl group, and more preferred are pyridyl group, quinolyl group and isoquinolyl group.

As for the above-mentioned B and C, if A is an unsubstituted or substituted phenylene group, B is a divalent condensed polycyclic aromatic hydrocarbon group or C is a monovalent heterocyclic group other than the pyridyl group. Here, as the monovalent heterocyclic group other than a pyridyl group, it is desired to use a nitrogen-containing aromatic heterocyclic group having a condensed polycyclic structure.

As the nitrogen-containing heterocyclic group having the condensed polycyclic structure, there can be exemplified quinolyl group, isoquinolyl group, indolyl group, carbazolyl group, carbolinyl group, benzoxazolyl group, benzothiazolyl group, quinoxalyl group, benzimidazolyl group, napthylidinyl group, phenanthrolynyl group and acrydinyl group. Among them, more preferred are quinolyl group, isoquinolyl group, indolyl group, carbolynyl group, quinoxalyl group, benzimidazolyl group, naphthylidinyl group and phenanthrolinyl group, and most preferred are quinolyl group and isoquinolyl group.

As for the above-mentioned B and C, if A is an unsubstituted or substituted phenylene group, the most desirable embodiment is that B is a single bond and C is a monovalent heterocyclic group (specifically, nitrogen-containing heterocyclic group) other than a pyridyl group.

The benzotriazole derivatives of the present invention represented by the above general formula (1) are novel compounds and can be synthesized by, for example, the methods described below.

That is, a 2-aminoarylazobenzene derivative having an aromatic heterocyclic group as a substituent is synthesized from a 1,2-diaminobenzene derivative having substituents equivalent to $Ar^1$ and $Ar^2$ in the general formula (1) and a nitroaryl derivative having an aromatic heterocyclic group as a substituent according to a known method. The thus synthesized compound is subjected to the oxidative cyclization reaction (e.g., see Aust. J. Chem., 45, 371 (1992)) with a iodobenzene diacetate to thereby synthesize a 2-arylbenzotriazole derivative (benzotriazole derivative of the present invention) having an aromatic heterocyclic group as a substituent.

The substituent can also be introduced into the benzotriazole ring structure by using a 1,2-diaminobenzene derivative that has a halogen atom such as bromine as a substituent.

That is, the 2-arylbenzotriazole derivative having a halogen atom as a substituent is synthesized, and the thus obtained halogen-substituted derivative and various arylboronic acid derivatives are subjected to the cross-coupling reaction such as the Suzuki coupling (e.g., see Synth. Commun., 11, 513 (1981)) to synthesize the benzotriazole derivative of the present invention.

Further, the 2-arylbenzotriazole derivative having the aromatic heterocyclic group as the substituent is brominated with an imide N-bromosuccinate to synthesize a brominated 2-arylbenzotriazole derivative having the aromatic heterocyclic group as the substituent, which is similarly subjected to the cross-coupling reaction such as the Suzuki coupling together with various arylboronic acid derivatives to thereby synthesize the benzotriazole derivative of the present invention.

Here, upon changing the reagent and conditions for bromination, it is allowed to obtain bromo-substituents having different positions of substitution. It is, further, possible to introduce not only the benzotriazole ring structure but also the bromine atom, and the compounds having benzotriazole derivatives of the present invention can be synthesized through the similar cross-coupling reaction such as the Suzuki coupling.

The synthesized compounds can be refined by the column chromatography, by the adsorption method using silica gel, active carbon or active clay, by the recrystallization with a solvent or by the crystallization method.

Described below are concrete examples of the benzotriazole derivatives of the invention obtained as described above to which only, however, the invention is in no way limited.

Here, No. 1 is missing from the following compounds.

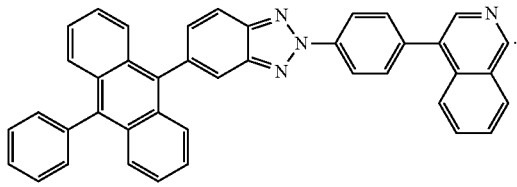

(Compound 2)

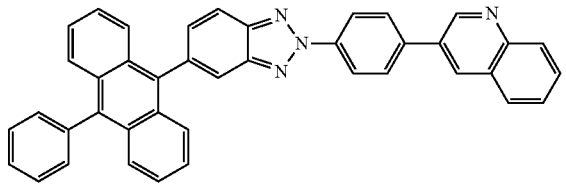

(Compound 3)

-continued
(Compound 4)
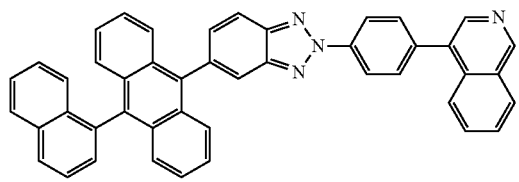
(Compound 5)
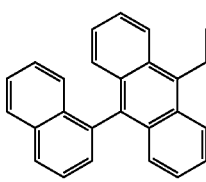
(Compound 6)
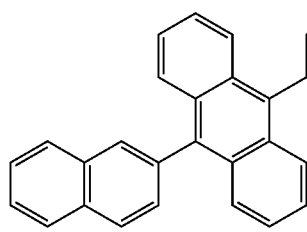
(Compound 7)
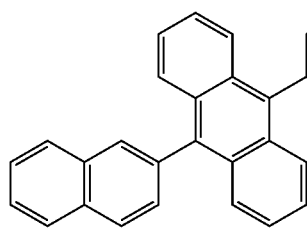
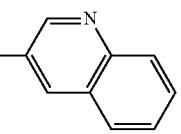
(Compound 8)
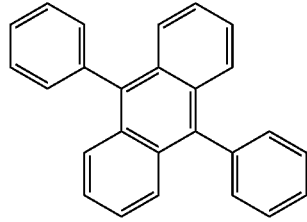
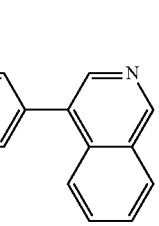
(Compound 9)
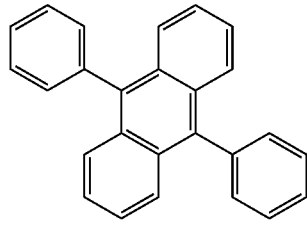
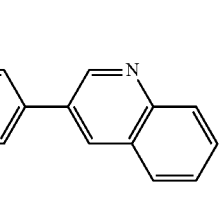
(Compound 10)
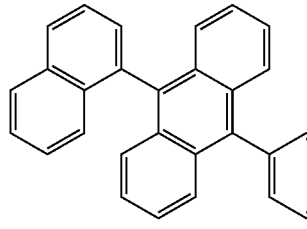
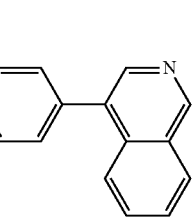
(Compound 11)
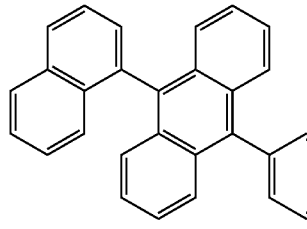
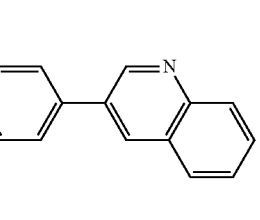

-continued
(Compound 12)
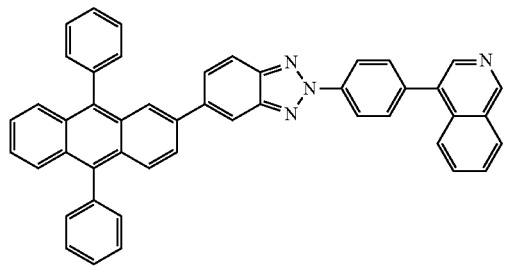
(Compound 13)
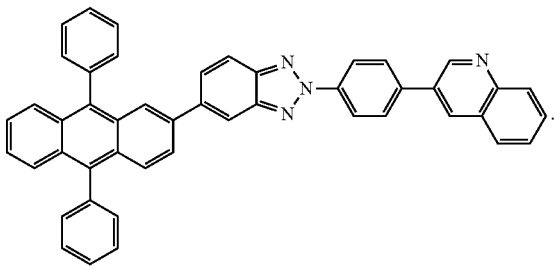
(Compound 14)
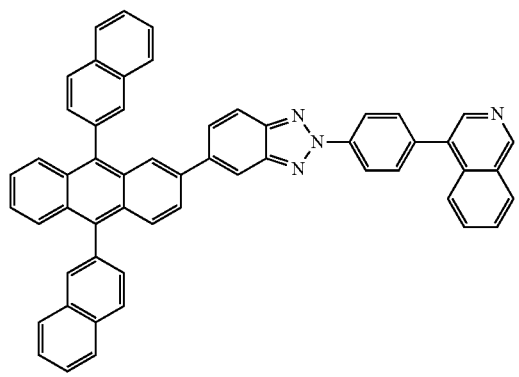
(Compound 15)
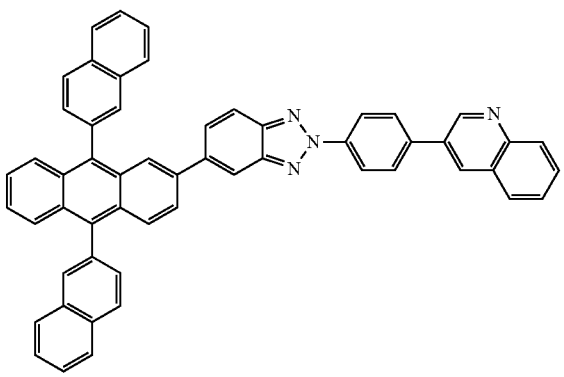
(Compound 16)
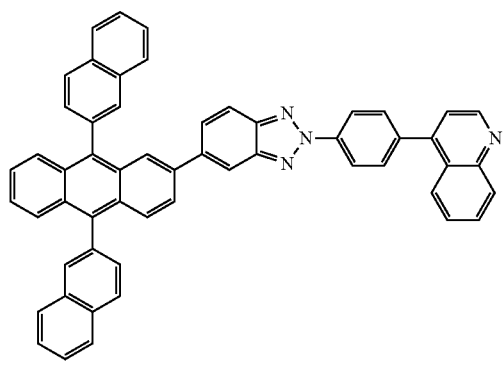
(Compound 17)
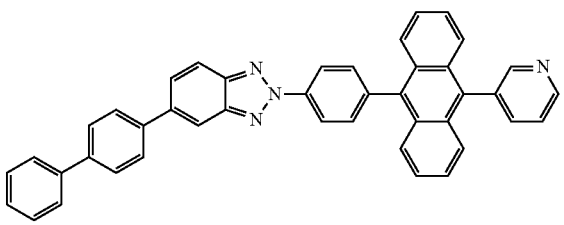
(Compound 18)
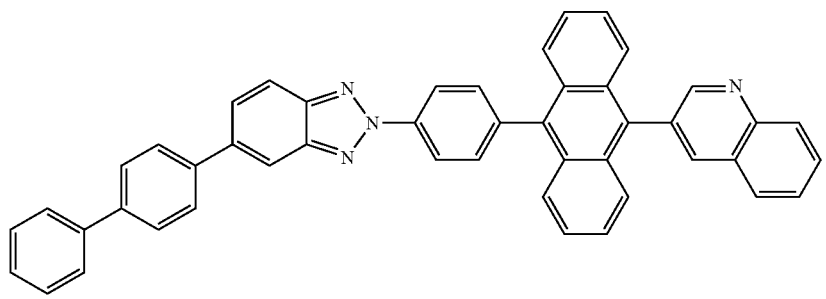

-continued
(Compound 19)
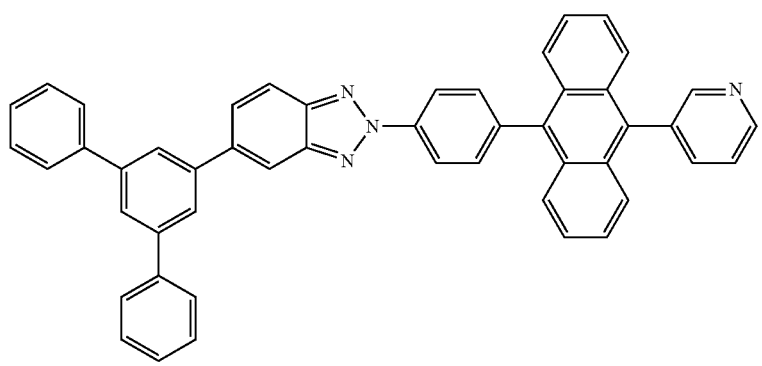
(Compound 20)
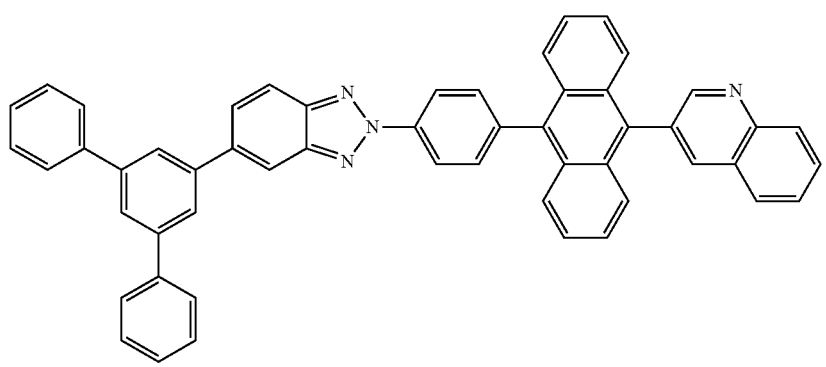
(Compound 21) (Compound 22)
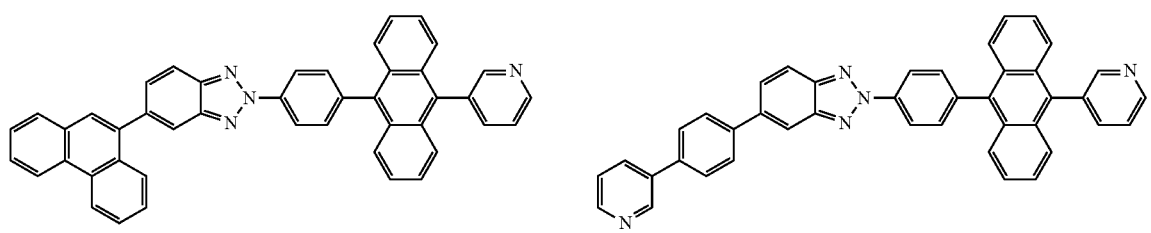
(Compound 23)
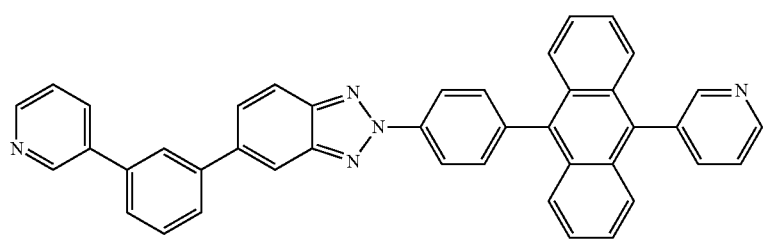
(Compound 24)
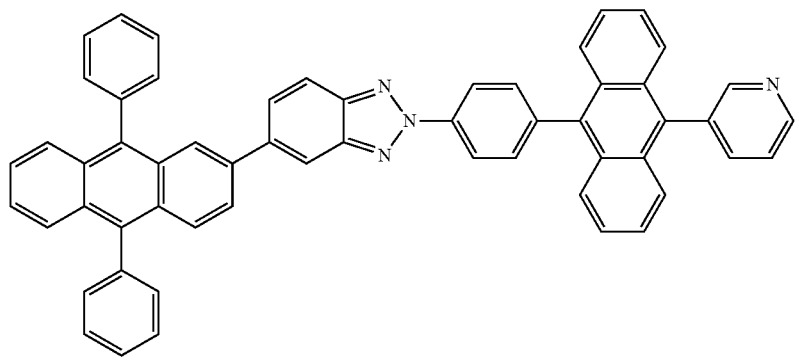

(Compound 25)
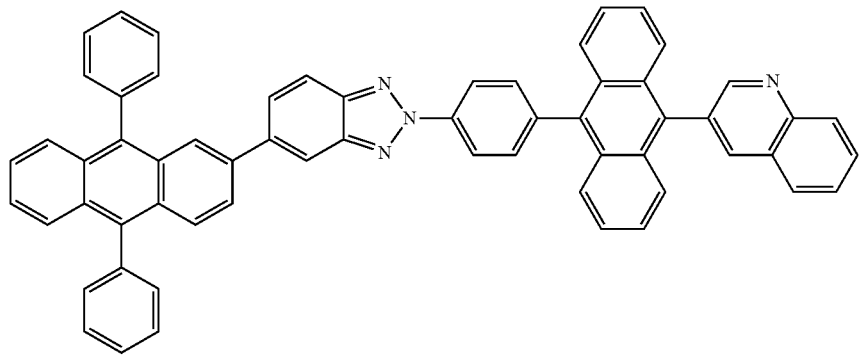
(Compound 26)
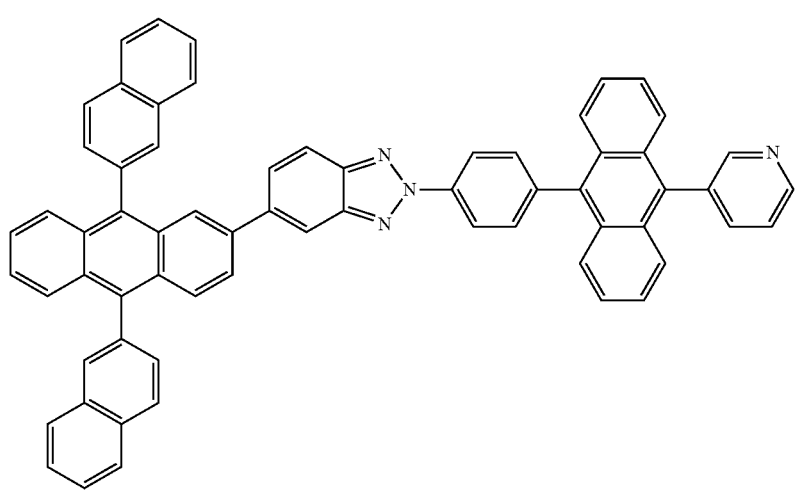
(Compound 27)
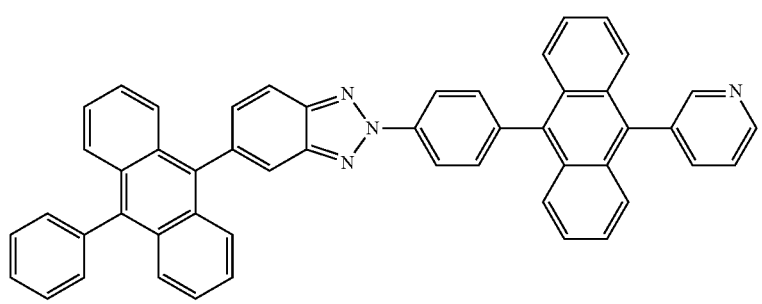
(Compound 28)
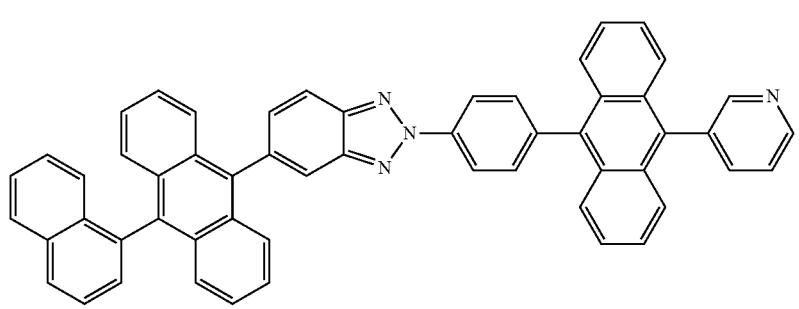

-continued
(Compound 29)
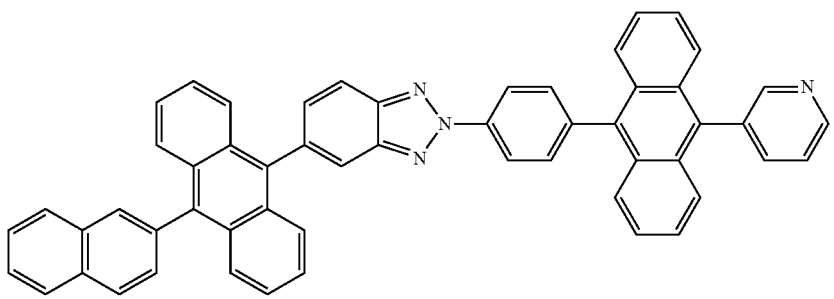
(Compound 30) (Compound 31)
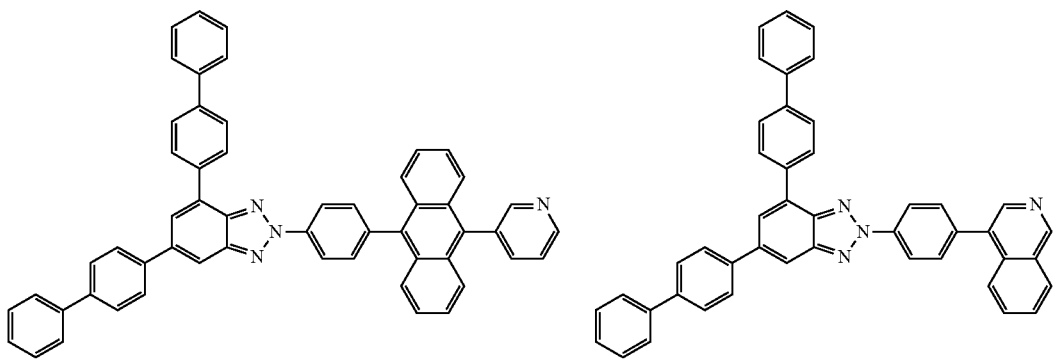
(Compound 32) (Compound 33)
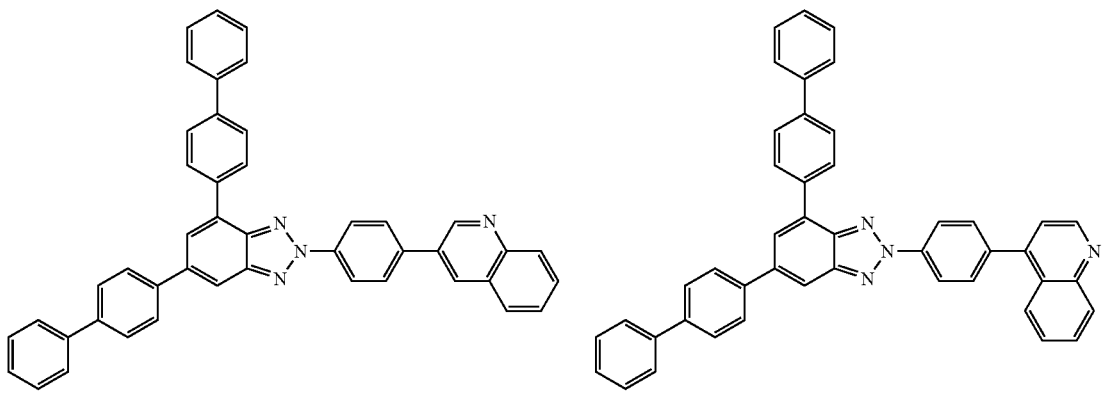
(Compound 34) (Compound 35)
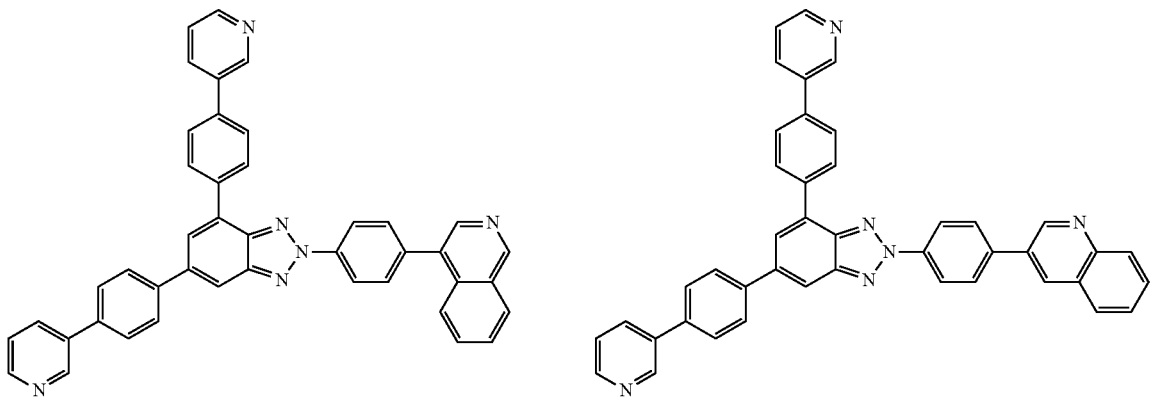

(Compound 36)
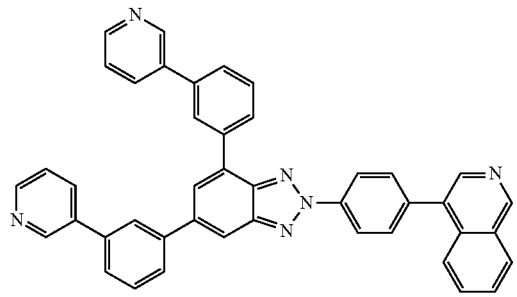
(Compound 37)
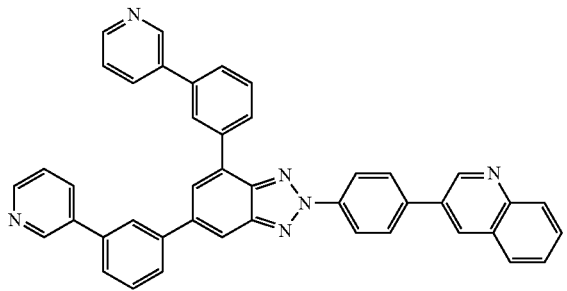
(Compound 38)
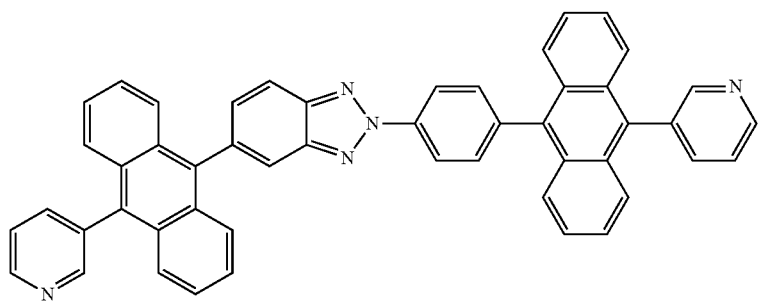
(Compound 39)
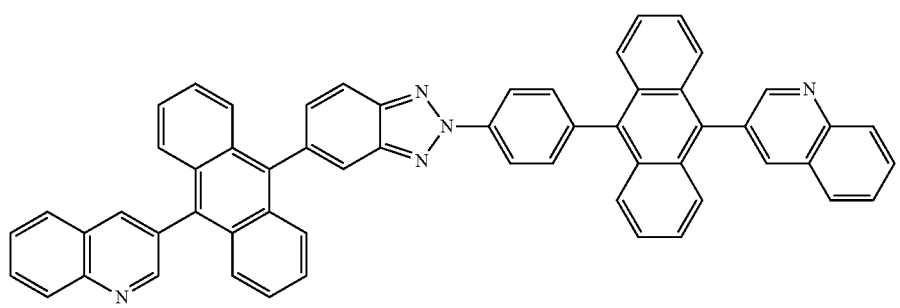
(Compound 40)
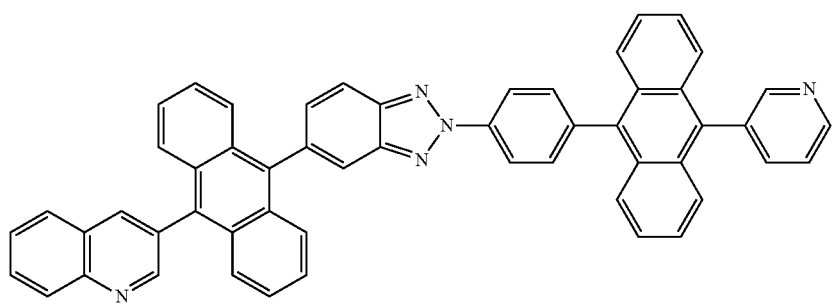
(Compound 41)
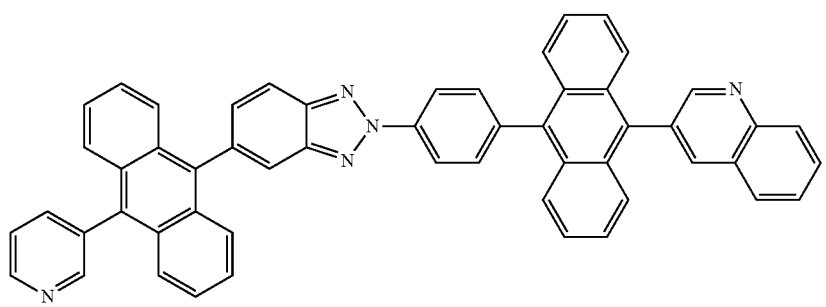

-continued
(Compound 42)
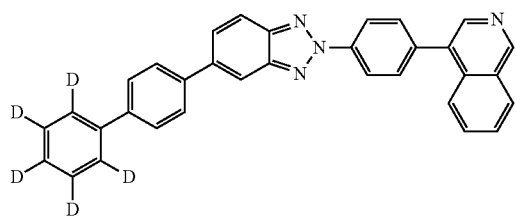
(Compound 43)
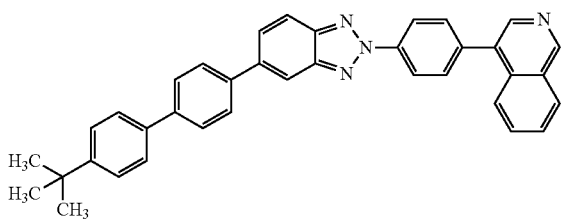
(Compound 44)
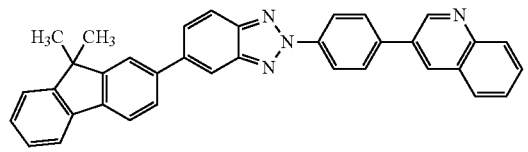
(Compound 45)
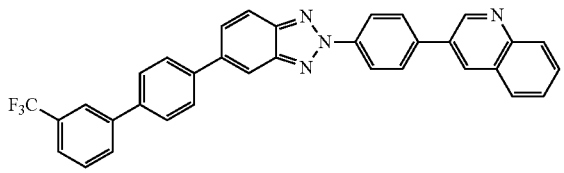
(Compound 46)
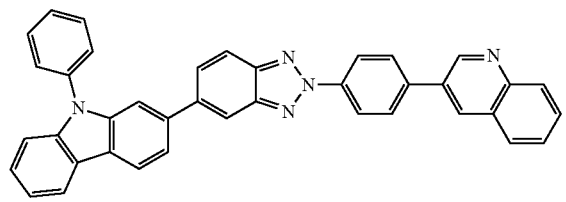
(Compound 47)
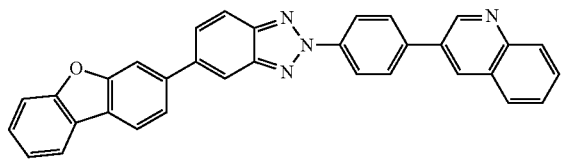
(Compound 48)
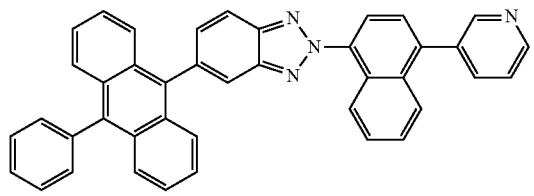
(Compound 49)
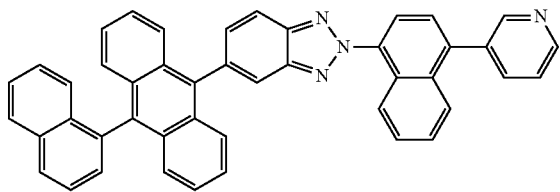
(Compound 50)
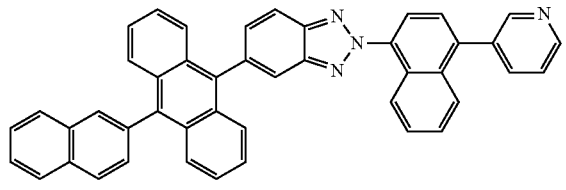
(Compound 51)
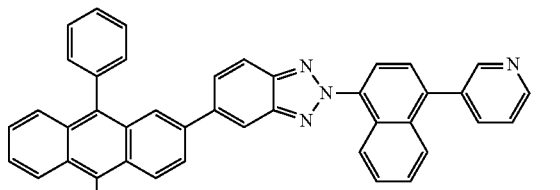
(Compound 52)
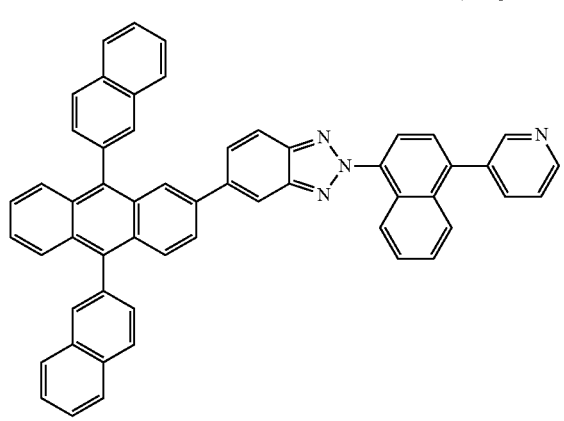
(Compound 53)
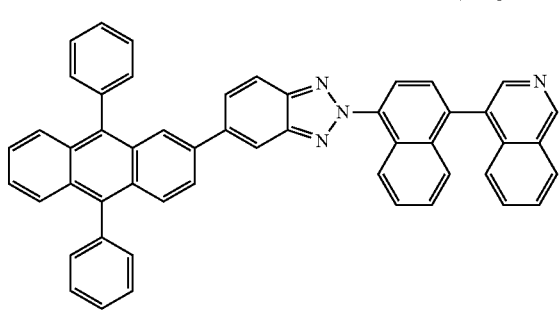

-continued
(Compound 54)
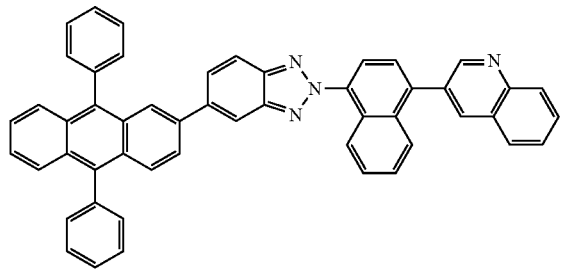
(Compound 55)
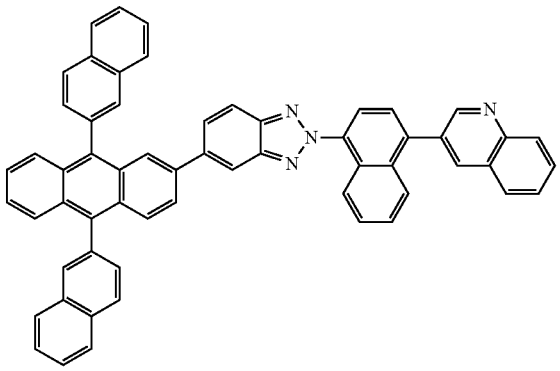
(Compound 56)
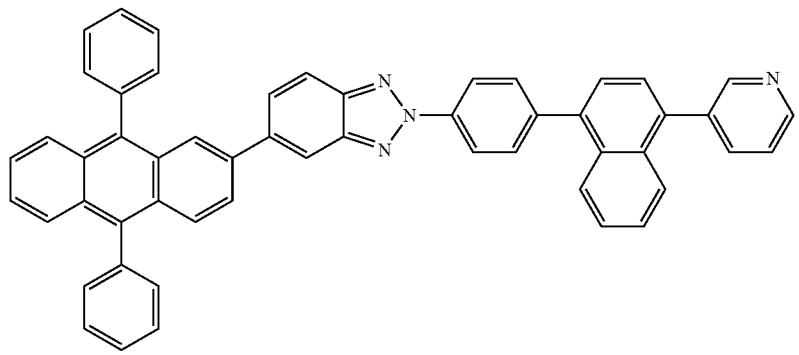
(Compound 57)
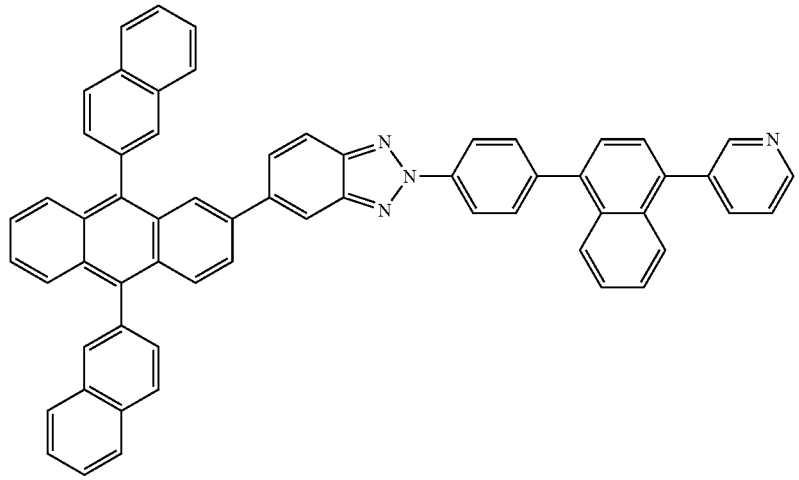
(Compound 58)
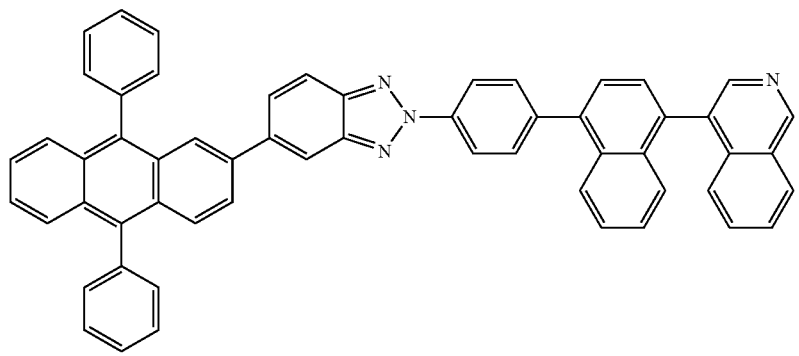

(Compound 59)

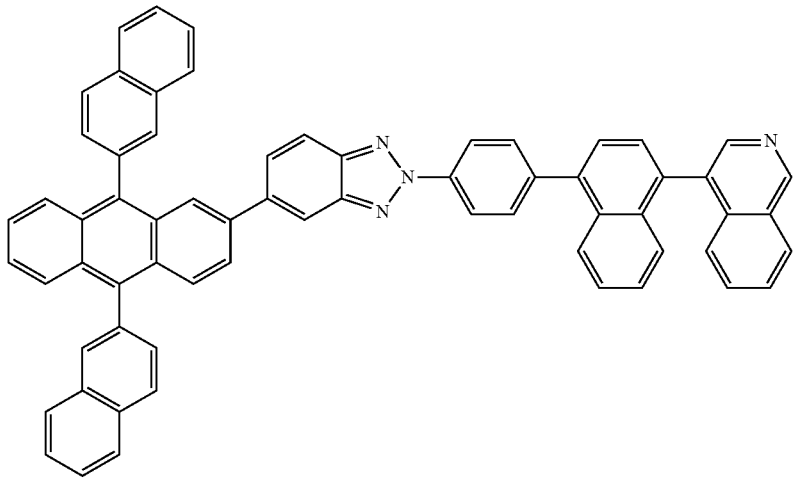

(Compound 60)

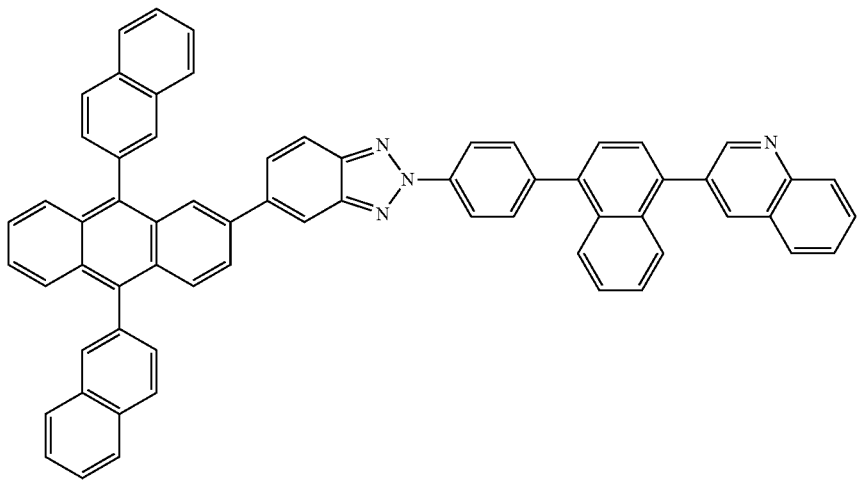

(Compound 61)

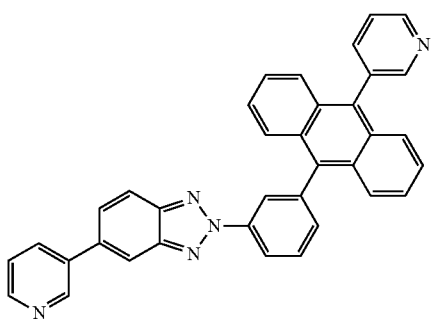

(Compound 62)

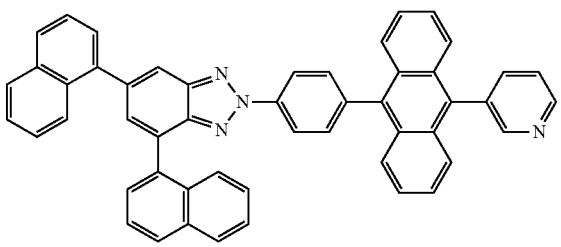

The above-mentioned benzotriazole derivatives of the present invention have high melting points and high glass transition points (Tg), are capable of forming thin films having excellent heat resistance and are capable of maintaining amorphous state with stability. Besides, these compounds permit electrons to drift faster than the conventional electron-transporting materials, have excellent hole-blocking power, remain stable in the state of thin films and therefore, can be used for fabricating an organic EL device that features elongated service life.

The hole-blocking power of the benzotriazole derivatives of the invention can be evaluated in terms of work functions. As also demonstrated in Examples appearing later, the work functions are measured by forming a thin film of 100 nm on an ITO substrate and by using an ionization potential-measuring apparatus (model PYS-202 manufactured by Sumitomo Heavy Industries, Ltd.).

<Organic EL Devices>

Figure 7:
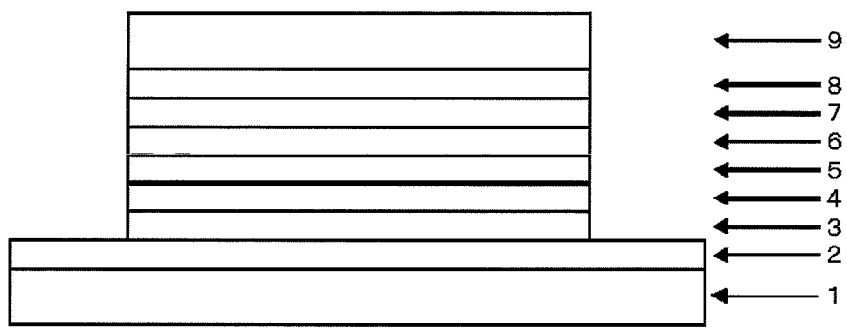
FIG. 7 is a view illustrating the structure of layers of an organic EL device of the present invention.

The organic EL device having the organic layer formed by using the above benzotriazole derivative of the present invention has a structure as shown, for example, in FIG. 7.

Namely, a transparent anode 2, a hole injection layer 3, a hole-transporting layer 4, a luminous layer 5, a hole-blocking layer 6, an electron-transporting layer 7, an electron injection layer 8 and a cathode 9 are formed on a glass substrate 1 (which may be any transparent substrate such as transparent resin substrate or the like substrate).

The organic EL device to which the benzotriazole derivative of the present invention is applied is not limited to the one of the above layer structure, as a matter of course, and an electron-blocking layer and the like can be formed between the hole-transporting layer 4 and the luminous layer 5. Or the organic EL device may have a simplified layer structure omitting the electron injection layer 8 or the hole injection layer 3. For instance, some layers can be omitted from the above multilayer structure. For instance, the organic EL device can be fabricated in a simple layer structure having the anode 2, hole-transporting layer 4, luminous layer 5, electron-transporting layer 7 and cathode 9 formed on the substrate 1.

That is, the benzotriazole derivative of the invention is preferably used as a material for forming organic layers (e.g., luminous layer 5, hole-blocking layer 6, electron-transporting layer 7 and electron injection layer 8) between the anode 2 and the cathode 9.

In the organic EL device, the transparent anode 2 may be formed by using an electrode material which has been known per se, i.e., by vapor-depositing an electrode material having a large work function, such as ITO or gold on the substrate 1 (transparent substrate such as glass substrate or the like).

Further, the hole injection layer 3 can be formed on the transparent anode 2 by using the materials that have been known per se, such as those described below.

- Porphyrin compound as represented by copper phthalocyanine;
- Triphenylamine derivative of the star burst type;
- Arylamine having a structure coupled via a single bond or a divalent group without hetero atom (e.g., trimer or tetramer of triphenylamine);
- Acceptor-type heterocyclic compounds such as hexacyanoazatriphenylene; and
- High molecular materials of the application type, such as poly(3,4-ethylenedioxythiophene) (PEDOT), poly(styrene sulfonate) (PSS), etc.

The layer (thin film) can be formed by using the above materials relying not only upon the vacuum evaporation method but also upon the known methods such as spin-coating method or ink-jet method. The layers described below, too, can similarly be formed by the vacuum evaporation, the spin-coating or the ink-jet method.

The hole-transporting layer 4, too, can be formed on the hole injection layer 3 by using a hole-transporting material that has been known per se. Representative examples of the hole-transporting materials are: benzidine derivatives such as,

- N,N'-diphenyl-N,N'-di(m-tolyl)benzidine (hereinafter abbreviated as TPD);
- N,N'-diphenyl-N,N'-di($\alpha$-naphthyl)benzidine (hereinafter abbreviated as NPD); and
- N,N,N',N'-tetrabiphenylylbenzidine; and amine derivatives such as,
- 1,1-bis[4-(di-4-tolylamino)phenyl]cyclohexane (hereinafter abbreviated as TAPC);
- various triphenylamine trimers and tetramers; and the above-mentioned application-type high molecular materials that can also be used for forming the hole injection layer.

The compounds for forming the hole-transporting layer may be used alone to form a film or may be used being mixed together in two or more kinds to form a film. Or the above compounds may be used in one kind or in a plurality of kinds to form a plurality of layers, and a multiplicity of films formed by laminating such layers may be used as a hole-transporting layer.

It is, further, allowable to form a layer that serves as both the hole injection layer 3 and the hole-transporting layer 4. The hole injection• transporting layer can be formed by being coated with a high molecular material such as poly (3,4-ethylenedioxythiophene) (hereinafter abbreviated as PEDOT) or polystyrene sulfonate (hereinafter abbreviated as PSS).

In forming the hole-transporting layer 4 (the same holds for the hole injection layer 3, too), the material usually used for forming the layer may, further, be P-doped with a trisbromophenylaminehexachloroantimony or the like. It is also allowable to form the hole-transporting layer 4 (or the hole injection layer 3) by using a high molecular compound having a basic skeleton of TPD.

Further, as the electron-blocking layer (that can be formed between the hole-transporting layer 4 and the luminous layer 5) that has not been shown, there can be used a known electron-blocking compound having the electron-blocking action, such as carbazole derivative or a compound that has a triphenylsilyl group and a triarylamine structure. Described below are concrete examples of the carbazole derivative and the compound having the triarylamine structure.

<Carbazole Derivatives>
- 4,4',4"-Tri(N-carbazolyl)triphenylamine (hereinafter abbreviated as TCTA);
- 9,9-Bis[4-(carbazole-9-il)phenyl]fluorene;
- 1,3-Bis(carbazole-9-il)benzene (hereinafter abbreviated as mCP); and
- 2,2-Bis(4-carbazole-9-ilphenyl)adamantane (hereinafter abbreviated as Ad-Cz);

<Compounds Having a Triarylamine Structure>
- 9-[4-(Carbazole-9-il)phenyl]-9-[4-(triphenylsilyl)phenyl]-9H-fluorene;

The electron-blocking layer is formed by using one, two or more kinds of the above known electron-blocking materials. It is also allowable to form a plurality of layers by using one or a plurality of kinds of the electron-blocking materials, and use a multiplicity of films formed by laminating such layers as the electron-blocking layer.

The luminous layer 5 of the organic EL device can be formed by using the benzotriazole derivative of the invention as the luminous material. The luminous layer 5 can also be formed by using luminous materials such as a metal complex of a quinolynol derivative as represented by Alq$_3$, various metal complexes such as of zinc, beryllium and aluminum, anthracene derivatives, bisstyrylbenzene derivatives, pyrene derivatives, oxazole derivatives and polyparaphenylenevinylene derivatives.

It is also allowable to constitute the luminous layer 5 by using a host material and a dopant material.

As the host material in this case, there can be used thiazole derivative, benzimidazole derivative and polydialkylfluorene derivative in addition to the above luminous materials.

As the dopant material, there can be used quinacridone, cumalin, rubrene, perylene and derivatives thereof, benzopyran derivatiive, rhodamine derivative and aminostyryl derivative.

The luminous layer 5, too, can be formed in a single-layer structure by using one or two or more kinds of the luminous materials, or in a multi-layer structure by laminating a plurality of layers.

It is, further, allowable to form the luminous layer 5 by using a phosphorescent luminous material as the luminous material.

As the phosphorescent luminous material, there can be used a phosphorescent luminous body of a metal complex such as of iridium or platinum. For example, there can be used a green luminous phosphor such as Ir(ppy)₃, a blue luminous phosphor such as Flrpic or Flr₆, and a red luminous phosphor such as Btp₂Ir(acac). These phosphorescent luminous materials are used by being doped in the hole injection• transporting host material or in the electron-transporting host material.

As the hole injection• transporting host material, there can be used carbazole derivatives such as 4,4'-di(N-carbazolyl) biphenyl (hereinafter abbreviated as CBP), TCTA or mCP in addition to using the benzotriazole derivative of the present invention.

As the electron-transporting host material, there can be used p-bis(triphenylsilyl)benzene (hereinafter abbreviated as UGH2) or 2,2',2''-(1,3,5-phenylene)-tris(1-phenyl-1H-benzimidazole) (hereinafter abbreviated as TPBI).

To avoid the concentration quenching, the host material is desirably doped with the phosphorescent luminous material in an amount in a range of 1 to 30% by weight relative to the whole luminous layer relying on the vacuum coevaporation.

As the luminous material, further, it is also allowable to use a material that emits retarded fluorescence, such as CDCB derivative like PIC-TRZ, CC2TA, PXZ-TRZ or 4CzIPN (see Appl. Phys. Let., 98, 083302 (2011)).

The hole-blocking layer 6 can also be formed between the luminous layer 5 and the electron-transporting layer 7 by using a known compound having the hole-blocking action in addition to using the benzotriazole derivative of the present invention.

As the known compounds having the hole-blocking action, there can be exemplified the following compounds.

Phenanthroline derivatives such as bathocuproin (hereinafter abbreviated as BCP) and the like;
Metal complexes of quinolinol derivatives such as aluminum(III)bis(2-methyl-8-quinolinato)-4-phenylphenolate (hereinafter abbreviated as BAlq) and the like;
Various rare earth complexes;
Triazole derivatives;
Triazine derivatives; and
Oxadiazole derivatives.

These materials can also be used for forming the electron-transporting layer 7 that will be described below. Moreover, the hole-blocking layer 6 and the electron-transporting layer 7 can be formed as one layer.

The hole-blocking layer 6, too, can be formed in the structure of a single layer or of a laminate of a multiplicity of layers, the layers being formed by using one kind or two or more kinds of the above-mentioned compounds having hole-blocking action.

The electron-transporting layer 7 can be formed by using electron-transporting compounds that have been known per se. such as metal complexes of quinolinol derivatives like Alq₃ and BAlq, various metal complexes, triazole derivatives, triazine derivatives, oxadiazole derivatives, thiadiazole derivatives, carbodiimide derivatives, quinoxaline derivatives, phenanthroline derivatives and silole derivatives in addition to using the benzotriazole derivatives of the present invention.

The electron-transporting layer 7, too, can be formed in the structure of a single layer or of a laminate of a multiplicity of layers, the layers being formed by using one kind or two or more kinds of the above-mentioned electron-transporting compounds.

The electron injection layer 8, too, can be formed by using known compounds, i.e., by using alkali metal salts such as lithium fluoride and cesium fluoride, alkaline earth metal salts such as magnesium fluoride, and metal oxides such as aluminum oxide in addition to using the benzotriazole derivatives of the present invention.

Further, the electron injection layer 8 or the electron-transporting layer 7 may be formed by using materials that have usually been used for forming these layers but that are N-doped with a metal such as cesium or the like.

As the cathode 9 of the organic EL device, there can be used an electrode material having a low work function, such as aluminum, or an electrode material of an alloy having a lower work function, such as magnesium-silver alloy, magnesium-indium alloy or aluminum-magnesium alloy.

The organic EL device forming at least one of the organic layers (e.g., electron injection layer 8, electron-transporting layer 7, hole-blocking layer 6 or luminous layer 5) by using the benzotriazole derivative of the present invention, features a high luminous efficiency, a high power efficiency, a low practical driving voltage, a low luminance start voltage and very excellent durability.

EXAMPLES

The invention will now be more concretely described by way of Examples to which only, however, the invention is in no way limited unless the gist of the invention is exceeded.

Example 1

Synthesis of a 4-[4-{5-(9,10-diphenyl-anthracene-2-il)benzotriazole-2-il}phenyl]isoquinoline (Synthesis of the Compound 12)

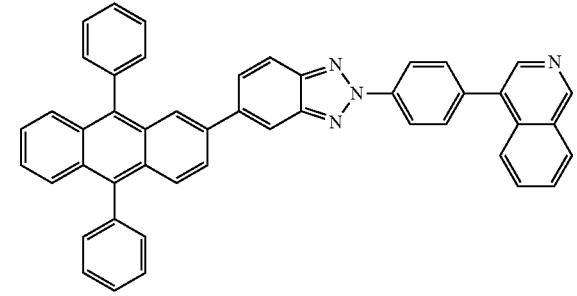

(Compound 12)

The ingredients of the following recipe:

| | |
|---|---|
| 1-Bromo-4-nitrobenzene | 50 g, |
| (Isoquinoline-4-il)boronic acid pinacol ester | 69.4 g, |
| 2M Potassium carbonate aqueous solution | 309 ml, |
| Toluene | 200 ml, |
| Ethanol | 40 ml and |
| Tetrakistriphenylphosphine palladium (0) | 11.0 g | were put into a reaction vessel purged with nitrogen, and were heated and refluxed for 14 hours with stirring. The reaction solution was concentrated, and the precipitated crystals were picked up by filtration. Through the dispersion washing with an isopropanol, there was 52.5 g of a grey powder of 4-(4-nitrophenyl) isoquinoline crystals (yield, 84.8%).

Next, the ingredients of the following recipe:

| 4-(4-Nitrophenyl) isoquinoline obtained above | 5.0 g, |
|---|---|
| 4-Bromo-1,2-diaminobenzene | 3.7 g, |
| Caustic soda | 1.6 g and |
| Toluene | 50 ml | were put into the reaction vessel purged with nitrogen, and were heated and refluxed for 7 hours with stirring. 100 Milliliters of toluene was added thereto to extract the reaction solution which was then concentrated under a reduced pressure and was refined by the column chromatography to obtain 3.4 g of a red powder of 5-bromo-2-{4-(isoquinoline-4-il)phenylazo}phenylamine crystals (yield, 42.1%).

Further, the ingredients of the following recipe:

| 5-Bromo-2-{4-(isoquinoline-4-il)phenylazo} phenylamine obtained above | 4.0 g, |
|---|---|
| Iodobenzene diacetate | 4.8 g and |
| Toluene | 100 ml | were put into the reaction vessel purged with nitrogen, and were stirred at 74° C. for one hour. The organic layer was picked up by the separating operation, was concentrated under a reduced pressure and was refined by the column chromatography to obtain 2.4 g of a white powder of 5-bromo-2-{4-(isoquinoline-4-il)phenyl}-2H-benzotriazole crystals (yield, 60.2%).

Next, the ingredients of the following recipe:

| 5-Bromo-2-{4-(isoquinoline-4-il)phenyl}-2H-benzotriazole | 4.0 g, |
|---|---|
| (9,10-Diphenylanthracene-2-il) boric acid | 4.5 g, |
| 2M Potassium carbonate aqueous solution | 15 ml, |
| Toluene | 30 ml, |
| Ethanol | 12 ml and |
| Tetrakistriphenylphosphine palladium (0) | 0.1 g | were put into the reaction vessel purged with nitrogen, and were heated and refluxed for 8.5 hours with stirring. The organic layer was picked up by the separating operation, was concentrated under a reduced pressure and was refined by the column chromatography to obtain 5.8 g of a yellow powder of 4-[4-{5-(9,10-diphenyl-anthracene-2-il)benzotriazole-2-il}phenyl]isoquinoline (compound 12) (yield 82.7%).

The obtained yellow powder was identified for its structure by the NMR. FIG. 1 shows the results of the $^1$H-NMR measurement.

The following 30 signals of hydrogen were detected by the $^1$H-NMR (CDCl$_3$).

δ (ppm)=9.31 (1H)
8.56 (1H)
8.52 (1H)
8.10 (1H)
8.08 (1H)
8.03 (1H)
7.98 (1H)
7.95 (1H)
7.85 (1H)
7.74-7.53 (18H)
7.37 (1H)
7.43 (1H)
7.35 (1H)

Example 2

Synthesis of a 3-[4-{5-(9,10-diphenylanthracene-2-il)benzotriazole-2-il}phenyl]quinoline (Synthesis of the Compound 13)

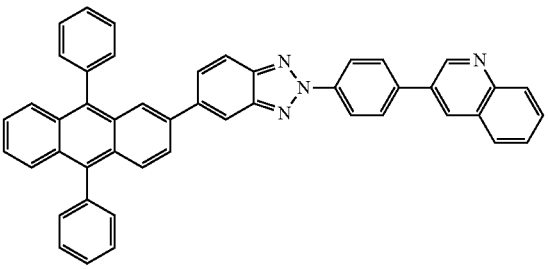

(Compound 13)

The ingredients of the following recipe:

| 1-Bromo-4-nitrobenzene | 50 g, |
|---|---|
| (Quinoline-3-il)boronic acid | 47.1 g, |
| 2M Potassium carbonate aqueous solution | 309 ml, |
| Toluene | 200 ml, |
| Ethanol | 40 ml and |
| Tetrakistriphenylphosphine palladium (0) | 11.0 g | were put into a reaction vessel purged with nitrogen, and were heated and refluxed for 14 hours with stirring. The reaction solution was concentrated, and the precipitated crystals were picked up by filtration. Through the dispersion washing with an isopropanol, there was obtained 55.2 g of a grey powder of 3-(4-nitrophenyl) quinoline crystals (yield, 89.1%).

Next, the ingredients of the following recipe:

| 3-(4-Nitrophenyl)quinoline obtained above | 5.0 g, |
|---|---|
| 4-Bromo-1,2-diaminobenzene | 3.7 g, |
| Caustic soda | 1.6 g and |
| Toluene | 50 ml | were put into the reaction vessel purged with nitrogen, and were heated and refluxed for 7 hours with stirring. 100 Milliliters of toluene was added thereto to extract the reaction solution which was then concentrated under a reduced pressure and was refined by the column chromatography to obtain 3.8 g of a red powder of 5-bromo-2-{4-(quinoline-3-il)phenylazo}phenylamine crystals (yield, 47.1%).

Further, the ingredients of the following recipe:

| 5-Bromo-2-{4-(quinoline-3-il)phenylazo}phenylamine obtained above | 4.0 g, |
|---|---|
| Iodobenzene diacetate | 4.8 g and |
| Toluene | 100 ml | were put into the reaction vessel purged with nitrogen, and were stirred at 74° C. for one hour. The organic layer was picked up by the separating operation, was concentrated under a reduced pressure and was refined by the column chromatography to obtain 2.8 g of a white powder of 5-bromo-2-{4-(quinoline-3-il)phenyl}-2H-benzotriazole crystals (yield, 70.2%).

Next, the ingredients of the following recipe:

| | |
|---|---|
| 5-Bromo-2-{4-(quinoline-3-il)phenyl}-2H-benzotriazole obtained above | 4.0 g, |
| (9,10-Diphenylanthracene-2-il) boric acid | 4.5 g, |
| 2M Potassium carbonate aqueous solution | 15 ml, |
| Toluene | 30 ml, |
| Ethanol | 12 ml and |
| Tetrakistriphenylphosphine palladium (0) | 0.1 g | were put into the reaction vessel purged with nitrogen, and were heated and refluxed for 8.5 hours with stirring. The organic layer was picked up by the separating operation, was concentrated under a reduced pressure and was refined by the column chromatography to obtain 5.7 g of a yellow powder of 3-[4-{5-(9,10-diphenylanthracene-2-il)benzotri-azole-2-il}phenyl]quinoline (compound 13) (yield 82.6%).

Figure 2:
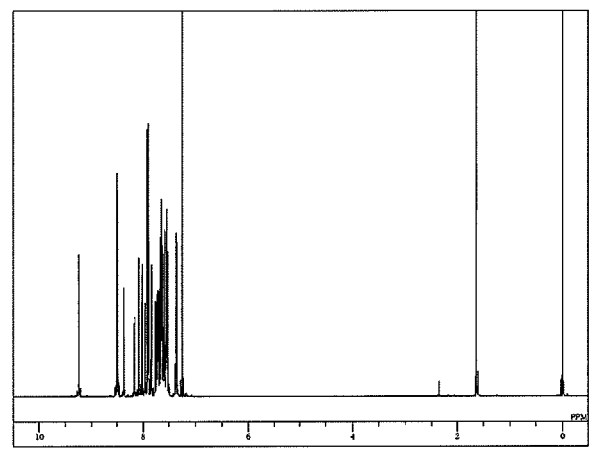
FIG. 2 is a $^1$H-NMR chart of a compound (compound 13) of Example 2.

The obtained yellow powder was identified for its structure by the NMR. FIG. 2 shows the results of the $^1$H-NMR measurement.

The following 30 signals of hydrogen were detected by the $^1$H-NMR (CDCl$_3$).

δ (ppm)=9.31 (1H)
8.56 (1H)
8.52 (2H)
8.10 (1H)
8.08 (1H)
8.03 (1H)
7.98 (1H)
7.96 (1H)
7.85 (1H)
7.73-7.53 (18H)
7.37 (1H)
7.35 (1H)

Example 3

Synthesis of a 4-[4-[5-{9,10-di(naphthalene-2-il)anthracene-2-il}benzotriazole-2-il]phenyl]isoquinoline (Synthesis of the Compound 14)

The ingredients of the following recipe:

| | |
|---|---|
| 5-Bromo-2-{4-(isoquinoline-4-il)phenyl}-2H-benzotriazole synthesized in Example 1 | 4.0 g, |
| {9,10-Di(naphthalene-2-il)anthracene-2-il)boronic acid | 5.6 g, |
| 2M Potassium carbonate aqueous solution | 15 ml, |
| Toluene | 30 ml and |
| Ethanol | 12 ml | were put into the reaction vessel purged with nitrogen, and were aerated with the nitrogen gas for 60 minutes with stirring.

Next, 0.1 g of the tetrakistriphenylphosphine palladium (0) was added thereto, and the mixture was heated and refluxed for 10.5 hours with stirring. The organic layer was picked up by the separating operation, was concentrated under a reduced pressure and was refined by the column chromatography to obtain 6.6 g of a yellow powder of 4-[4-[5-{9,10-di(naphthalene-2-il)anthracene-2-il}benzotriazole-2-il]phenyl]isoquinoline (compound 14) (yield 88.5%).

Figure 3:
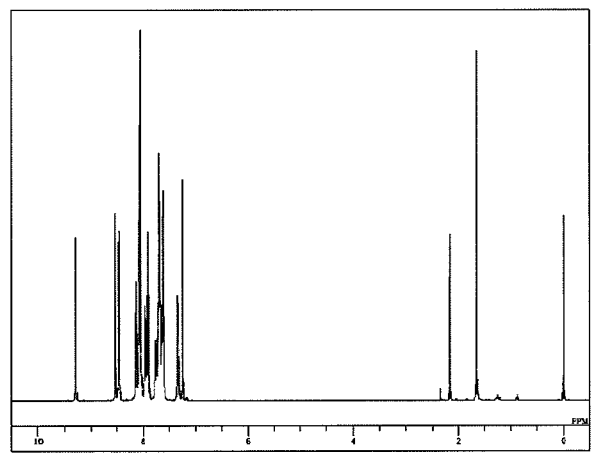
FIG. 3 is a $^1$H-NMR chart of a compound (compound 14) of Example 3.

The obtained yellow powder was identified for its structure by the NMR. FIG. 3 shows the results of the $^1$H-NMR measurement.

The following 34 signals of hydrogen were detected by the $^1$H-NMR (CDCl$_3$).

δ (ppm)=9.29 (1H)
8.47 (2H)
8.13 (1H)
8.08 (1H)
8.06-8.05 (8H)
7.96 (1H)
7.91 (1H)
7.90 (1H)
7.76 (1H)
7.71-7.61 (15H)
7.73 (2H)

Example 4

Synthesis of a 3-[4-[5-({9,10-di(naphthalene-2-il)anthracene-2-il}benzotriazole-2-il]phenyl]quinoline (Synthesis of the Compound 15)

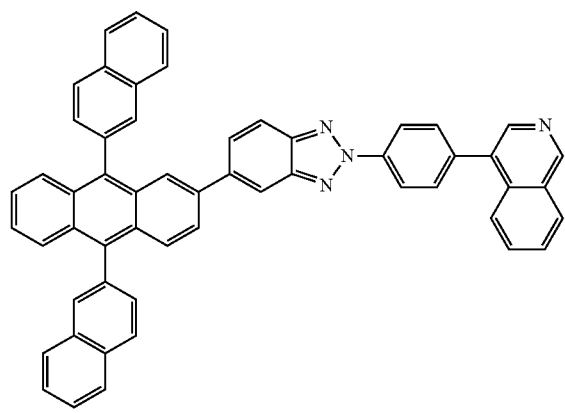

(Compound 14)

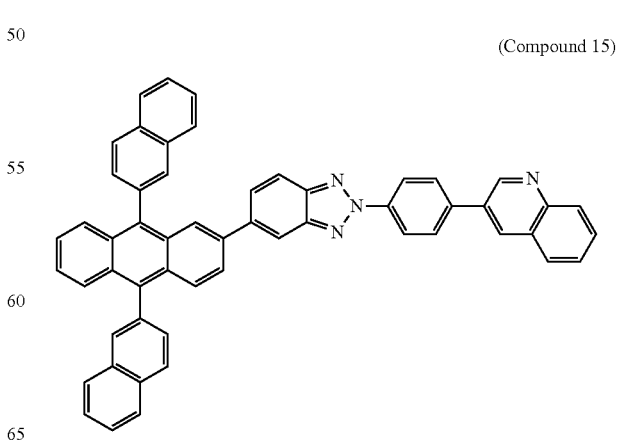

(Compound 15)

The ingredients of the following recipe:

| | |
|---|---|
| 5-Bromo-2-{4-(quinoline-3-il)phenyl}-2H-benzotriazole synthesized in Example 2 | 4.0 g, |
| {9,10-Di(naphthalene-2-il)anthracene-2-il)boronic acid | 5.6 g, |
| 2M Potassium carbonate aqueous solution | 15 ml, |
| Toluene | 30 ml and |
| Ethanol | 12 ml | were put into the reaction vessel purged with nitrogen, and were aerated with the nitrogen gas for 60 minutes with stirring.

Next, 0.1 g of the tetrakistriphenylphosphine palladium (0) was added thereto, and the mixture was heated and refluxed for 10.5 hours with stirring. The organic layer was picked up by the separating operation, was concentrated under a reduced pressure and was refined by the column chromatography to obtain 6.7 g of a yellow powder of 3-[4-[5-{9,10-di(naphthalene-2-il)anthracene-2-il}benzotriazole-2-il]phenyl]quinoline (compound 15) (yield 89.80).

Figure 4:
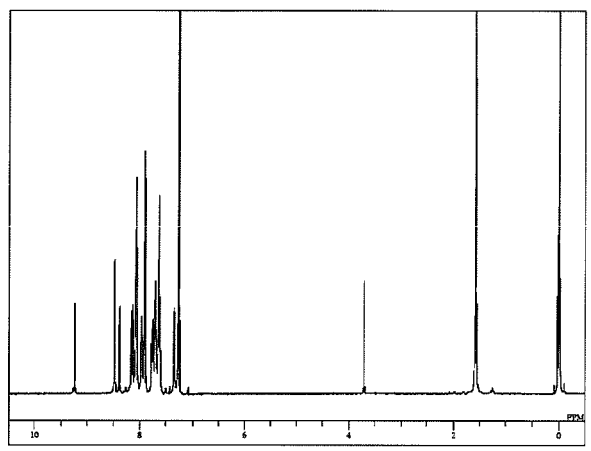
FIG. 4 is a $^1$H-NMR chart of a compound (compound 15) of Example 4.

The obtained yellow powder was identified for its structure by the NMR. FIG. 4 shows the results of the $^1$H-NMR measurement.

The following 34 signals of hydrogen were detected by the $^1$H-NMR (CDCl$_3$).

δ (ppm)=9.24 (1H)
8.49 (2H)
8.39 (1H)
8.17 (1H)
8.15 (1H)
8.13 (1H)
8.08-8.06 (6H)
7.97 (1H)
7.96 (1H)
7.92 (1H)
7.89 (4H)
7.78-7.60 (12H)
7.35 (2H)

Example 5

Synthesis of a 5-(biphenyl-4-il)-2-[4-{10-(pyridine-3-il)anthracene-9-il}phenyl]-2H-benzotriazole
(Synthesis of the Compound 17)

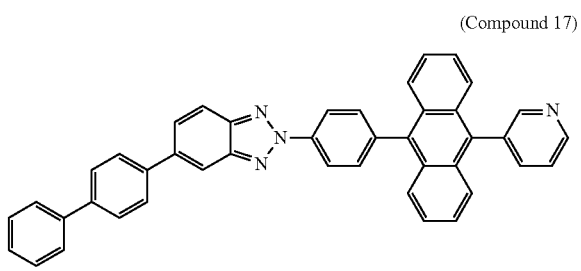 [SMILES: c1ccc(-c2ccc(-c3ccc4nn(-c5ccc(-c6c7ccccc7c(-c7cccnc7)c7ccccc67)cc5)nc4c3)cc2)cc1]

(Compound 17)

The ingredients of the following recipe:

| | |
|---|---|
| 5-Bromo-2-(4-chlorophenyl)-2H-benzotriazole | 5.0 g, |
| 4-Biphenylboronic acid | 3.9 g, |
| 2M Potassium carbonate aqueous solution | 25 ml, |
| 1,4-Dioxane | 50 ml and |
| Tetrakistriphenylphosphine palladium (0) | 0.2 g | were put into a reaction vessel purged with nitrogen, and were heated and refluxed for 7 hours with stirring. The reaction solution was cooled down to room temperature, 100 ml of methanol was added thereto, and the precipitated coarse product was picked up by filtration. After washed with water, the coarse product was dispersion-washed with methanol, and there was obtained 4.8 g of a powder of 5-(biphenyl-4-il)-2-(4-chlorophenyl)-2H-benzotriazole crystals (yield, 77.4%).

Next, the ingredients of the following recipe:

| | |
|---|---|
| 5-(Biphenyl-4-il)-2-(4-chlorophenyl)-2H-benzotriazole obtained above | 2.8 g, |
| Bis(pinacholato) diboron | 2.2 g, |
| Potassium acetate | 2.1 g and |
| 1,4-Dioxane | 56 ml | were put into the reaction vessel purged with nitrogen, and were aerated with the nitrogen gas for 60 minutes.

Next, 0.16 g of a dichloromethane complex of [1,1'-bis(diphenylphosphino)ferrocene]palladium (II) dichloride (1:1) was added thereto, and the mixture was heated and stirred at 80° C. for 3 hours. The mixture was cooled down to room temperature, was concentrated and was refined by adsorption by using 100 ml of toluene and 50 g of silica gel. Next, through the dispersion washing with 100 ml of methanol, there was obtained 3.0 g of a white powder of 5-(biphenyl-4-il)-2-{4-(4,4,5,5-tetramethyl-[1,3,2]dioxaborolane-2-il)phenyl}-2H-benzotriazole crystals (yield, 54.3%).

Next, the ingredients of the following recipe:

| | |
|---|---|
| 5-(Biphenyl-4-il)-2-{4-(4,4,5,5-tetramethyl-[1,3,2]dioxaborolane-2-il)phenyl}-2H-benzotriazole obtained above | 1.0 g, |
| 10-(Pyridine-3-il)-9-bromoanthracene | 0.7 g, |
| 2M Potassium carbonate aqueous solution | 3.3 ml, |
| 1,4-Dioxane | 10 ml and |
| Tetrakistriphenylphosphine palladium (0) | 0.02 g | were put into the reaction vessel purged with nitrogen, and were heated and refluxed for 7 hours with stirring. The mixture was cooled down to room temperature, 100 ml of methanol was added thereto, and the precipitated coarse product was picked up by filtration. Through the washing with water and dispersion washing with methanol, there was obtained 0.88 g of a faintly yellow powder of 5-(biphenyl-4-il)-2-[4-{10-(pyridine-3-il)anthracene-9-il}phenyl]-2H-benzotriazole (compound 17) crystals (yield, 69.8%).

Figure 5:
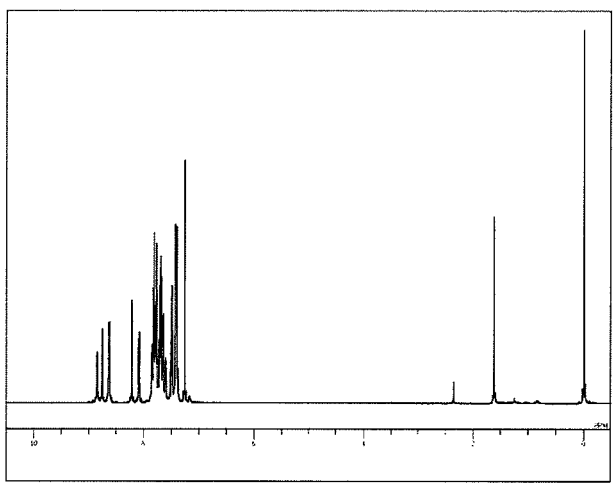
FIG. 5 is a $^1$H-NMR chart of a compound (compound 62) of Example 5.

The obtained faintly yellow powder of crystals was identified for its structure by the NMR. FIG. 5 shows the results of the $^1$H-NMR measurement.

The following 28 signals of hydrogen were detected by the $^1$H-NMR (CDCl$_3$).

δ (ppm)=8.85 (1H)
8.76 (1H)
8.64 (2H)
8.22 (1H)
8.09 (1H)

7.86-7.60 (15H)
7.49 (2H)
7.42-7.39 (5H)

Example 6

Synthesis of a 4,6-di(naphthalene-1-il)-2-[4-{10-(pyridine-3-il)anthracene-9-il}phenyl]-2H-benzotriazole (Synthesis of the Compound 62)

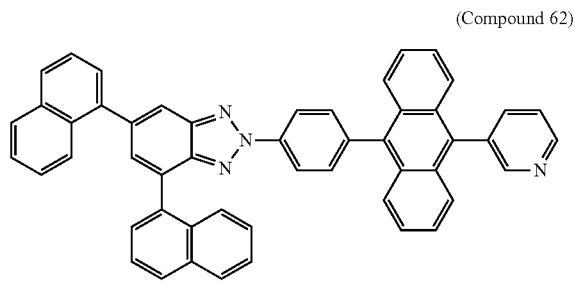 [SMILES: c1cncc(-c2c3ccccc3c(-c3ccc(-n4nc5cc(-c6cccc7ccccc67)cc(-c6cccc7ccccc67)c5n4)cc3)c3ccccc23)c1]

(Compound 62)

The ingredients of the following recipe:

| | |
|---|---|
| 4,6-Dibromo-2-(4-chlorophenyl)-2H-benzotriazole | 25.0 g, |
| 1-Naphthylboronic acid | 25.0 g, |
| 2M Potassium carbonate aqueous solution | 96 ml, |
| 1,4-Dioxane | 250 ml and |
| Tetrakistriphenylphosphine palladium (0) | 0.74 g | were put into the reaction vessel purged with nitrogen, and were heated and refluxed for 5 hours with stirring. The reaction product was concentrated and was refined by adsorption by using 200 ml of toluene and 50 g of silica gel. Thereafter, through the dispersion washing with 100 ml of methanol, there was obtained 25.8 g of a grey powder of 4,6-di(naphthalene-1-n)-2-(4-chlorophenyl)-2H-benzotriazole crystals (yield, 83.7%).

Next, the ingredients of the following recipe:

| | |
|---|---|
| 4,6-Di(naphthalene-1-il)-2-(4-chlorophenyl)-2H-benzotriazole obtained above | 12.0 g, |
| Bis(pinacholato) diboron | 9.5 g, |
| Potassium acetate | 7.4 g and |
| 1,4-Dioxane | 240 ml | were put into the reaction vessel purged with nitrogen, and were aerated with the nitrogen gas.

Next, 0.46 g of a dichloromethane complex of [1,1'-bis(diphenylphosphino)ferrocene]palladium (II) dichloride (1:1) was added thereto, and the mixture was heated and stirred at 90° C. for 5 hours. The mixture was cooled down to room temperature, was concentrated and was refined by the column chromatography to obtain 9.5 g of a faintly yellow powder of 4,6-di(naphthalene-1-il)-2-{4-(4,4,5,5-tetramethyl-[1,3,2]dioxaborolane-2-il)phenyl}-2H-benzotriazole crystals (yield, 66.6%).

Next, the ingredients of the following recipe:

| | |
|---|---|
| 4,6-Di(naphthalene-1-il)-2-{4-(4,4,5,5-tetramethyl-[1,3,2]dioxaborolane-2-il)phenyl}-2H-benzotriazole obtained above | 5.7 g, |
| 10-(Pyridine-3-il)-9-bromoanthracene | 3.3 g, |
| Potassium phosphate | 6.4 g, |
| Water | 14.2 ml and |
| 1,4-Dioxane | 142 ml | were put into the reaction vessel purged with nitrogen, and were aerated with the nitrogen gas for 60 minutes.

Next, 0.2 g of trisdibenzylideneacetonedipalladium and 0.1 g of tricyclohexylphosphine were added thereto, and the mixture was heated and refluxed for 4 hours with stirring. The mixture was cooled, 100 ml of toluene was added thereto, insoluble matters were removed by filtration, and the product was refined by adsorption by using 15 g of NH silica gel.

After concentrated, 50 ml of methanol was added, and the precipitated coarse product was picked up by filtration. There was obtained 5.4 g of a faintly yellow powder of 4,6-di(naphthalene-1-il)-2-[4-{10-(pyridine-3-il)anthracene-9-il}phenyl]-2H-benzotriazole (compound 62) crystals (yield, 77.7%).

Figure 6:
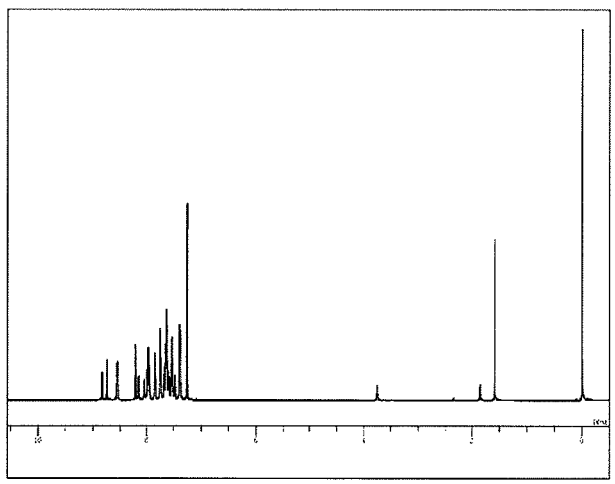
FIG. 6 is a $^1$H-NMR chart of a compound (compound 63) of Example 6.

The obtained faintly yellow powder of crystals was identified for its structure by the NMR. FIG. 6 shows the results of the $^1$H-NMR measurement.

The following 32 signals of hydrogen were detected by the $^1$H-NMR (CDCl$_3$).

δ (ppm)=8.84 (1H)
8.74 (1H)
8.56 (2H)
8.19 (1H)
8.15 (1H)
8.04 (1H)
7.94 (4H)
7.84 (2H)
7.76-7.74 (3H)
7.68-7.48 (12H)
7.41-7.37 (4H)

Example 7

By using a highly sensitive differential scanning calorimeter (DSC3100S manufactured by Bruker AXS K.K.), the compounds of the present invention obtained in the above Examples 1 to 6 were measured for their melting points and glass transition points. The results were as follows:

| | Melting points | Glass transition points |
|---|---|---|
| Compound of Ex. 1 | 286° C. | 153° C. |
| Compound of Ex. 2 | 334° C. | 150° C. |
| Compound of Ex. 3 | 238° C. | 183° C. |
| Compound of Ex. 4 | 340° C. | 182° C. |
| Compound of Ex. 5 | 318° C. | not observed |
| Compound of Ex. 6 | 205° C. | 174° C. |

As will be understood from the above results, the compounds of the present invention have glass transition points which are not lower than 100° C. and, specifically, not lower than 150° C., or which are not observed indicating that the thin films formed by using the compounds of the invention remain stable.

Moreover, the compounds have high melting points and large heat resistances. Specifically, the compounds of Examples 1 to 5 have differences between the melting points and the glass transition points of not less than 30° C. and are easy to handle.

Example 8

By using the compounds of the invention obtained in Examples 1 to 6, films were vapor-deposited in a thickness of 100 nm on an ITO substrate and were measured for their work functions by using an apparatus for measuring ionization potentials (Model PYS-202 manufactured by Sumitomo Heavy Industries, Ltd.). The results were as follows:

|  | Work functions |
|---|---|
| Compound of Ex. 1 | 5.91 eV |
| Compound of Ex. 2 | 5.94 eV |
| Compound of Ex. 3 | 5.85 eV |
| Compound of Ex. 4 | 5.91 eV |
| Compound of Ex. 5 | 6.22 eV |
| Compound of Ex. 6 | 6.21 eV |

As described above, the compounds of the present invention have values larger than a work function of 5.5 eV possessed by general hole-transporting materials such as NPD, TPD and the like, and have large hole-blocking powers.

Example 9

An organic EL device of a structure shown in FIG. 7 was fabricated in a manner as described below by using the compound obtained in Example 1.

First, a glass substrate 1 on which the ITO film has been formed in a thickness of 150 nm was washed with an organic solvent and was, thereafter, washed for its surfaces by an oxygen plasma treatment.

Thereafter, the glass substrate with the ITO electrode was placed in a vacuum evaporation machine, and the pressure therein was reduced down to 0.001 Pa or lower. Next, as the hole injection layer 3, a compound HIM-1 of the following structural formula was vapor-deposited at a deposition rate of 6 nm/min. in a thickness of 20 nm so as to cover the transparent anode 2.

Next, on the hole injection layer 3, a compound HTM-1 of the following structural formula was vapor-deposited as the hole-transporting layer 4 at a deposition rate of 6 nm/min. in a thickness of 40 nm.

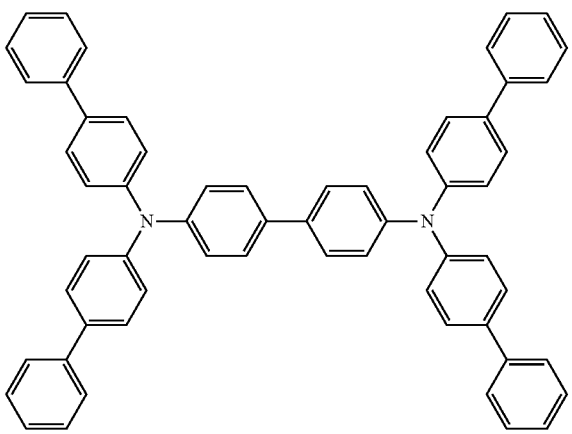

(HTM-1)

On the hole-transporting layer 4 formed above, the luminous layer 5 was formed in a thickness of 30 nm by two-way-depositing a compound EMD-1 of the following structural formula and a compound EMH-1 of the following structural formula at a deposition rate of EMD-1:EMH-1=5:95.

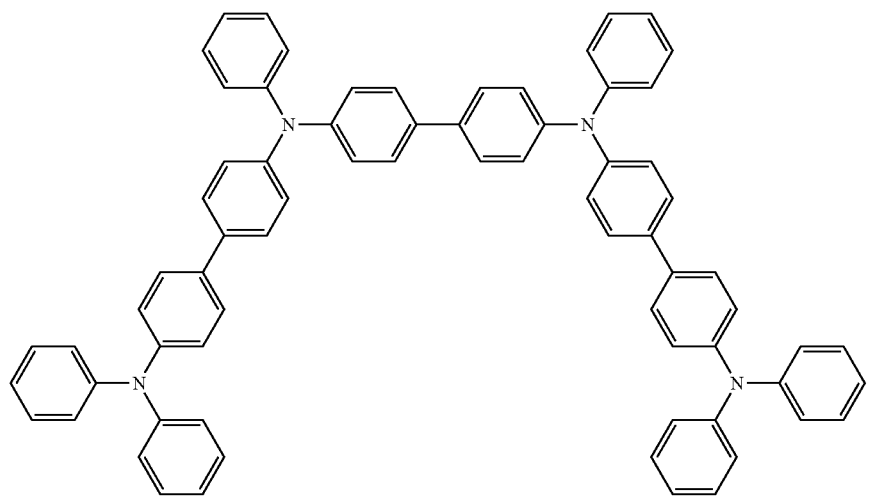

(HIM-1)

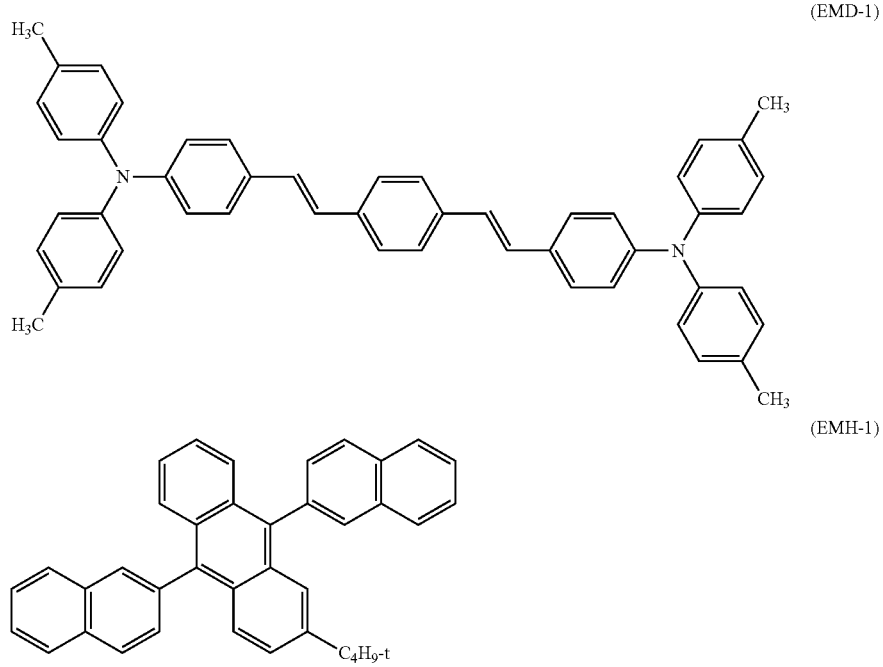

(EMD-1)

(EMH-1)

On the luminous layer 5, the compound 12 of the invention synthesized in Example 1 was vapor-deposited at a deposition rate of 6 nm/min. in a thickness of 30 nm so as to work as both the hole-blocking layer 6 and the electron-transporting layer 7.

Next, on the thus formed hole-blocking layer/electron-transporting layer 6 and 7, the electron injection layer 8 was formed in a thickness of 0.5 nm by vapor-depositing lithium fluoride at a deposition rate of 0.6 nm/min.

Finally, aluminum was vapor-deposited in a thickness of 150 nm to form the cathode 9. The thus fabricated organic EL device was measured for its properties in the atmosphere at normal temperature.

The thus fabricated organic EL device was impressed with a DC voltage to measure the luminous properties which were as collectively shown in Table 1.

Example 10

An organic EL device was fabricated in the same manner as in Example 9 but using the compound (compound 13) of Example 2 instead of using the compound (compound 12) of Example 1 to form the hole-blocking layer/electron-transporting layer in a thickness of 30 nm. The organic EL device was measured for its properties in the atmosphere at normal temperature.

The organic EL device was impressed with a DC voltage to measure the luminous properties which were as collectively shown in Table 1.

Example 11

An organic EL device was fabricated in the same manner as in Example 9 but using the compound (compound 14) of Example 3 instead of using the compound (compound 12) of Example 1 to form the hole-blocking layer/electron-transporting layer in a thickness of 30 nm. The thus fabricated organic EL device was measured for its properties in the atmosphere at normal temperature.

The thus fabricated organic EL device was impressed with a DC voltage to measure the luminous properties which were as collectively shown in Table 1.

Example 12

An organic EL device was fabricated in the same manner as in Example 9 but using the compound (compound 15) of Example 4 instead of using the compound (compound 12) of Example 1 to form the hole-blocking layer/electron-transporting layer in a thickness of 30 nm. The thus fabricated organic EL device was measured for its properties in the atmosphere at normal temperature.

The thus fabricated organic EL device was impressed with a DC voltage to measure the luminous properties which were as collectively shown in Table 1.

Example 13

An organic EL device was fabricated in the same manner as in Example 9 but using the compound (compound 62) of Example 6 instead of using the compound (compound 12) of Example 1 to form the hole-blocking layer/electron-transporting layer in a thickness of 30 nm. The thus fabricated organic EL device was measured for its properties in the atmosphere at normal temperature.

The thus fabricated organic EL device was impressed with a DC voltage to measure the luminous properties which were as collectively shown in Table 1.

Comparative Example 1

An organic EL device was fabricated in the same manner as in Example 9 but using the compound (ETM-1) of the following structural formula instead of using the compound (compound 12) of Example 1 to form the hole-blocking layer/electron-transporting layer in a thickness of 30 nm.

The thus fabricated organic EL device was measured for its properties in the atmosphere at normal temperature. The thus fabricated organic EL device was impressed with a DC voltage to measure the luminous properties which were as collectively shown in Table 1.

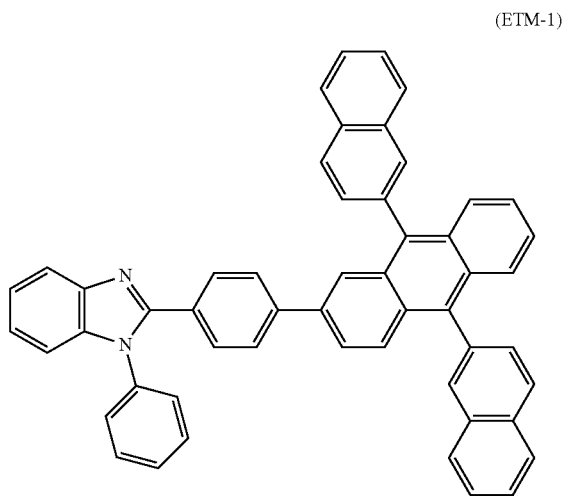 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

(ETM-1)

very larger than that of the ETM-1 of the above structural formula that is a widely used electron-transporting material.

INDUSTRIAL APPLICABILITY

The benzotriazole derivatives of the present invention have good electron injection property and excellent hole-blocking power, remain stable in their thin film state, and can be used as excellent compounds for fabricating the organic EL devices. Upon fabricating the organic EL devices by using the above compounds, further, it is allowed to attain a high luminous efficiency and power efficiency while lowering the practical driving voltage and improving the durability. Their use can, therefore, be expanded to, for example, domestic appliances and illumination equipment.

DESCRIPTION OF SYMBOLS 1 glass substrate
2 transparent anode
3 hole injection layer
4 hole-transporting layer
5 luminous layer
6 hole-blocking layer
7 electron-transporting layer
8 electron injection layer
9 cathode

TABLE 1

|  | Compound | Voltage [V] (@10 mA/cm$^2$) | Brightness [cd/m$^2$] (@10 mA/cm$^2$) | Current efficiency [cd/A] (@10 mA/cm$^2$) | Power efficiency [lm/W] (@10 mA/cm$^2$) |
|---|---|---|---|---|---|
| Example 9 | compound 12 | 4.95 | 832 | 8.32 | 5.28 |
| Example 10 | compound 13 | 5.03 | 836 | 8.36 | 5.22 |
| Example 11 | compound 14 | 5.05 | 845 | 8.45 | 5.25 |
| Example 12 | compound 15 | 5.10 | 843 | 8.43 | 5.19 |
| Example 13 | compound 62 | 4.98 | 840 | 8.40 | 5.21 |
| Comp. Ex. 1 | ETM-1 | 5.95 | 792 | 7.92 | 4.19 |

As for the driving voltage at a current density of 10 mA/cm$^2$ as shown in Table 1, the organic EL devices of Examples 9 to 13 of the invention have driving voltages of as low as 4.95 to 5.10 V as compared to 5.95 V of the organic EL device of Comparative Example 1 that uses the ETM-1 of the above structural formula. Further, the organic EL devices of Examples 9 to 13 of the invention exhibit current efficiencies of 8.32 to 8.45 cd/A which are great improvements over 7.92 cd/A of the organic EL device of Comparative Example 1.

Moreover, the organic EL devices of Examples 9 to 13 of the invention exhibit power efficiencies of 5.19 to 5.28 lm/W which are great improvements over 4.19 lm/W of the organic EL device of Comparative Example 1.

It will, therefore, be learned that the organic EL devices of the present invention are capable of achieving a great decrease in the practical driving voltages and great improvement in the luminous efficiency and power efficiency as compared to the devices that use the ETM-1 of the above structural formula that has been generally used as an electron-transporting material.

From a conspicuous decrease in the driving voltages attained by the organic EL devices using the benzotriazole derivatives of the present invention, it is presumed that the rate of electron migration in the benzotriazole derivatives is

The invention claimed is:
1. A Benzotriazole derivative represented by the following general formula (1),

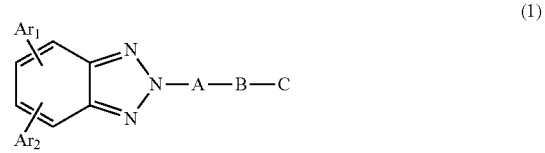

(1)

wherein,
Ar$^1$ is a monovalent aromatic hydrocarbon group or aromatic heterocyclic group,
Ar$^2$ is a hydrogen atom, a deuterium atom, or a monovalent aromatic hydrocarbon group or aromatic heterocyclic group,
A is a divalent aromatic hydrocarbon group,
B is a divalent condensed polycyclic aromatic hydrocarbon group or a single bond, and
C is a monovalent aromatic heterocyclic group,
and wherein if A is a phenylene group, B is a divalent condensed polycyclic aromatic hydrocarbon group or C is a monovalent aromatic heterocyclic group other than a pyridyl group.

2. The benzotriazole derivative according to claim 1, wherein A is a phenylene group in the general formula (1).

3. The benzotriazole derivative according to claim 2, wherein, in the general formula (1), B is a single bond and C is a group selected from quinolyl group, isoquinolyl group, indolyl group, carbazolyl group, carbolinyl group, benzoxazolyl group, benzothiazolyl group, quinoxalyl group, benzimidazolyl group, naphthyridinyl group, phenanthrolinyl group and acridinyl group.

4. The benzotriazole derivative according to claim 1, wherein B is a divalent condensed polycyclic aromatic hydrocarbon group in the general formula (1).

5. The benzotriazole derivative according to claim 4 wherein B is a naphthalenylene group in the general formula (1).

6. The benzotriazole derivative according to claim 4, wherein B is an anthracenylene group in the general formula (1).

7. The benzotriazole derivative according to claim 1, wherein A is a divalent condensed polycyclic aromatic hydrocarbon group in the general formula (1).

8. The benzotriazole derivative according to claim 7, wherein A is a naphthalenylene group in the general formula (1).

9. The benzotriazole derivative according to claim 7, wherein B is a single bond in the general formula (1).

10. An organic electroluminescent device having a pair of electrodes and at least one organic layer held therebetween, wherein at least the one organic layer contains the benzotriazole derivative of claim 1.

11. The organic electroluminescent device according to claim 10, wherein the at least one organic layer is an electron-transporting layer, a hole-blocking layer, a luminous layer or an electron injection layer.

* * * * *